United States Patent
Hmayakyan et al.

(10) Patent No.: US 7,891,462 B2
(45) Date of Patent: *Feb. 22, 2011

(54) STETHOSCOPE COVER AND DISPENSER THEREFOR

(76) Inventors: Samvel Hmayakyan, 607 N. Central Ave., Suite 303, Glendale, CA (US) 91203; Vahen Joakim, 659 W. Dryden St., Glendale, CA (US) 91202

(*) Notice: Subject to any disclaimer, the term of this patent is extended or adjusted under 35 U.S.C. 154(b) by 0 days.

This patent is subject to a terminal disclaimer.

(21) Appl. No.: 12/658,708

(22) Filed: Feb. 12, 2010

(65) Prior Publication Data

US 2010/0212995 A1    Aug. 26, 2010

Related U.S. Application Data

(63) Continuation-in-part of application No. 12/590,299, filed on Nov. 4, 2009, which is a continuation of application No. 12/217,007, filed on Jun. 30, 2008, now Pat. No. 7,614,478, which is a continuation-in-part of application No. 11/999,556, filed on Dec. 5, 2007, now Pat. No. 7,469,769.

(51) Int. Cl.
A61B 7/02 (2006.01)
B65H 1/08 (2006.01)
B65H 3/24 (2006.01)
B65G 59/06 (2006.01)
B65G 59/02 (2006.01)
G07F 11/16 (2006.01)

(52) U.S. Cl. .................. 181/131; 221/176; 221/232

(58) Field of Classification Search ........... 181/131, 181/130, 129; 600/528; 381/67; 379/452, 379/439; 221/266, 176, 263, 232, 268, 270, 221/246, 247, 255, 259

See application file for complete search history.

(56) References Cited

U.S. PATENT DOCUMENTS

| | | | | |
|---|---|---|---|---|
| 1,244,338 A * | 10/1917 | Johnson | 221/232 |
| 1,472,530 A * | 10/1923 | McComas | 379/447 |
| 2,152,174 A * | 3/1939 | Brunetti | 221/232 |
| 2,591,855 A * | 4/1952 | Nicholson | 221/232 |
| 2,640,347 A * | 6/1953 | Majeski | 70/456 R |
| 2,803,378 A * | 8/1957 | Gundling | 221/232 |
| 2,965,264 A * | 12/1960 | Silvia | 221/257 |
| 3,169,171 A * | 2/1965 | Wachs et al. | 379/452 |
| 3,393,831 A * | 7/1968 | Stewart | 221/232 |
| 3,578,207 A * | 5/1971 | Danow | 221/232 |
| 3,929,254 A * | 12/1975 | Artze | 221/30 |
| 4,000,831 A * | 1/1977 | House | 221/196 |
| 4,101,053 A * | 7/1978 | Mast, Jr. | 221/232 |

(Continued)

*Primary Examiner*—Edgardo San Martin
(74) *Attorney, Agent, or Firm*—James E. Brunton

(57) ABSTRACT

A protective cover for a stethoscope head and an apparatus for quickly and easily interconnecting the protective cover with the stethoscope head. The apparatus includes a cover-positioning device that positions the protective cover so that it can be quickly and easily interconnected with the stethoscope head. The cover positioning device includes a base having a planar portion and an upstanding rim connected to the planar portion. Following examination of the patient using the stethoscope with the protective head covering, the protective covering can be quickly and easily removed from the stethoscope head and suitably disposed of so as to prevent skin bacteria and like contaminants that may have contaminated the protective cover during patient examination, from undesirably being transmitted to the next patient.

11 Claims, 24 Drawing Sheets

U.S. PATENT DOCUMENTS

| | | | | |
|---|---|---|---|---|
| 4,779,759 | A * | 10/1988 | Seavey | 221/232 |
| 4,792,058 | A * | 12/1988 | Parker | 221/232 |
| 4,867,268 | A * | 9/1989 | Ulert | 181/137 |
| 4,871,046 | A * | 10/1989 | Turner | 181/131 |
| 4,876,715 | A * | 10/1989 | Neubert | 379/452 |
| 4,887,739 | A * | 12/1989 | Parker | 221/232 |
| 5,163,581 | A * | 11/1992 | Lombardi, Jr. | 221/256 |
| 5,428,193 | A * | 6/1995 | Mandiberg | 181/131 |
| 5,448,025 | A * | 9/1995 | Stark et al. | 181/131 |
| 5,466,897 | A * | 11/1995 | Ross et al. | 181/131 |
| 5,649,642 | A * | 7/1997 | Mabry et al. | 221/232 |
| 5,686,706 | A * | 11/1997 | Wurzburger | 181/131 |
| 5,808,244 | A * | 9/1998 | Knight et al. | 181/131 |
| 5,975,349 | A * | 11/1999 | Menes | 221/232 |
| 6,041,889 | A * | 3/2000 | Stark et al. | 181/131 |
| 6,135,314 | A * | 10/2000 | Menes | 221/232 |
| 6,206,134 | B1 * | 3/2001 | Stark et al. | 181/131 |
| 6,292,565 | B1 * | 9/2001 | Chamberlin et al. | 379/452 |
| 6,467,568 | B1 * | 10/2002 | Kemper | 181/131 |
| 6,499,560 | B1 * | 12/2002 | Lang et al. | 181/131 |
| 6,520,281 | B1 * | 2/2003 | Deslauriers et al. | 181/131 |
| 6,575,917 | B2 * | 6/2003 | Giroux et al. | 600/528 |
| 6,643,998 | B1 * | 11/2003 | Curtis et al. | 53/594 |
| 6,908,008 | B2 * | 6/2005 | Pugh | 221/135 |
| 7,117,971 | B1 * | 10/2006 | Cornacchia | 181/131 |
| 7,282,186 | B2 * | 10/2007 | Lake et al. | 422/300 |
| 7,320,413 | B2 * | 1/2008 | Fusi | 221/255 |
| 7,424,929 | B1 * | 9/2008 | Martinez | 181/131 |
| 7,469,769 | B1 * | 12/2008 | Hmayakyan et al. | 181/131 |
| 7,614,478 | B2 * | 11/2009 | Hmayakyan et al. | 181/131 |
| 2007/0045039 | A1 * | 3/2007 | Agahi et al. | 181/131 |
| 2010/0089688 | A1 * | 4/2010 | Hmayakyan et al. | 181/131 |

* cited by examiner

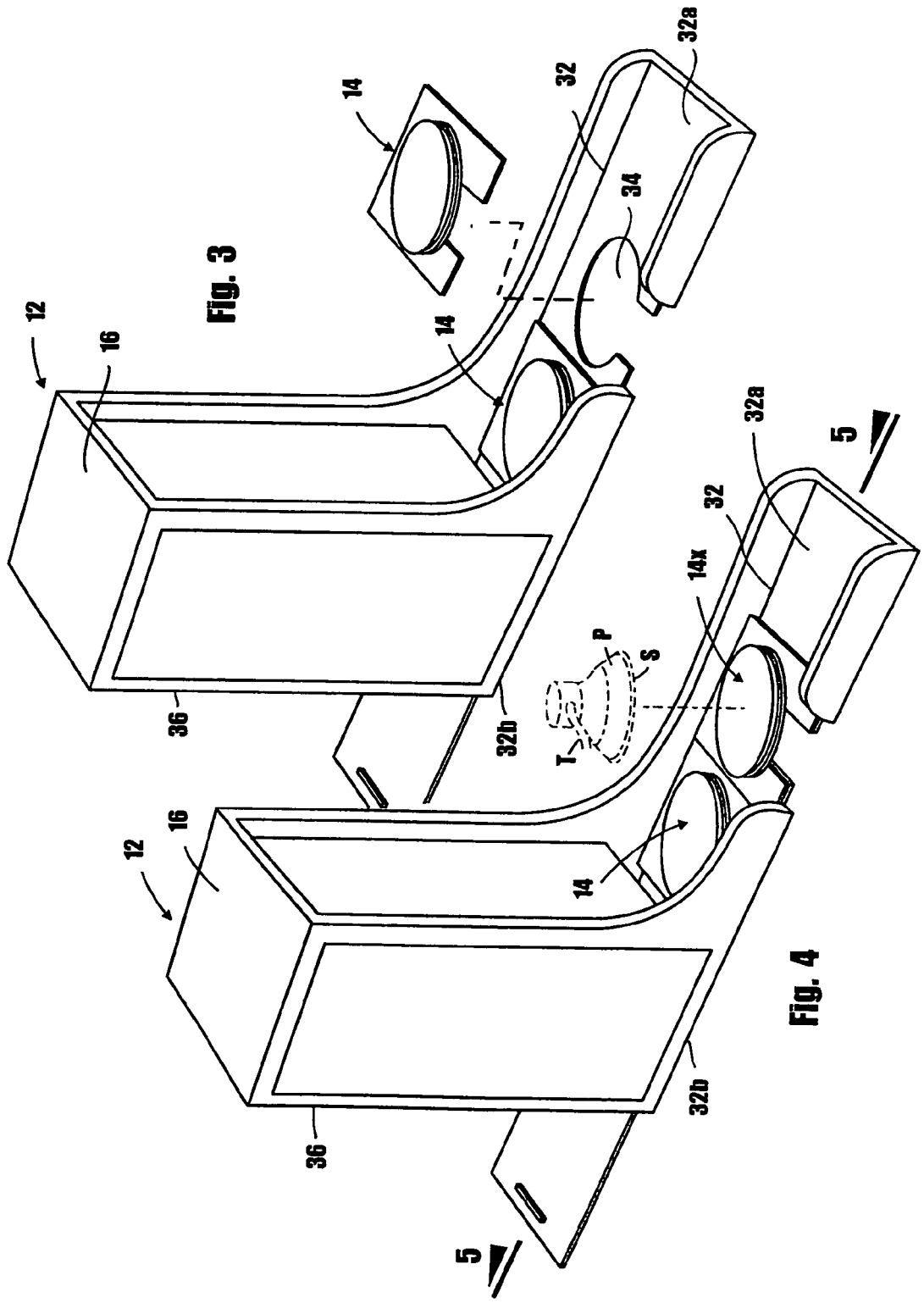

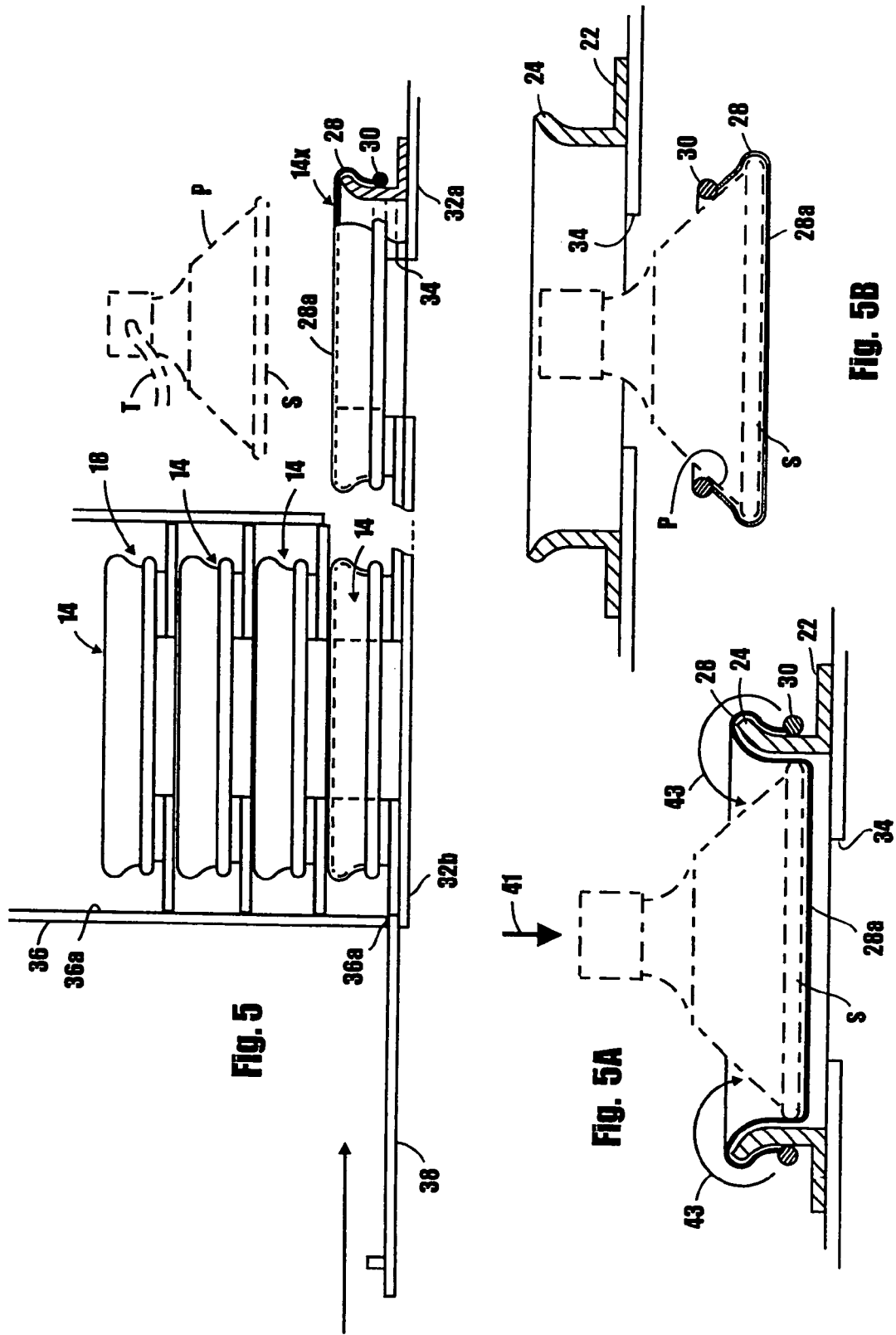

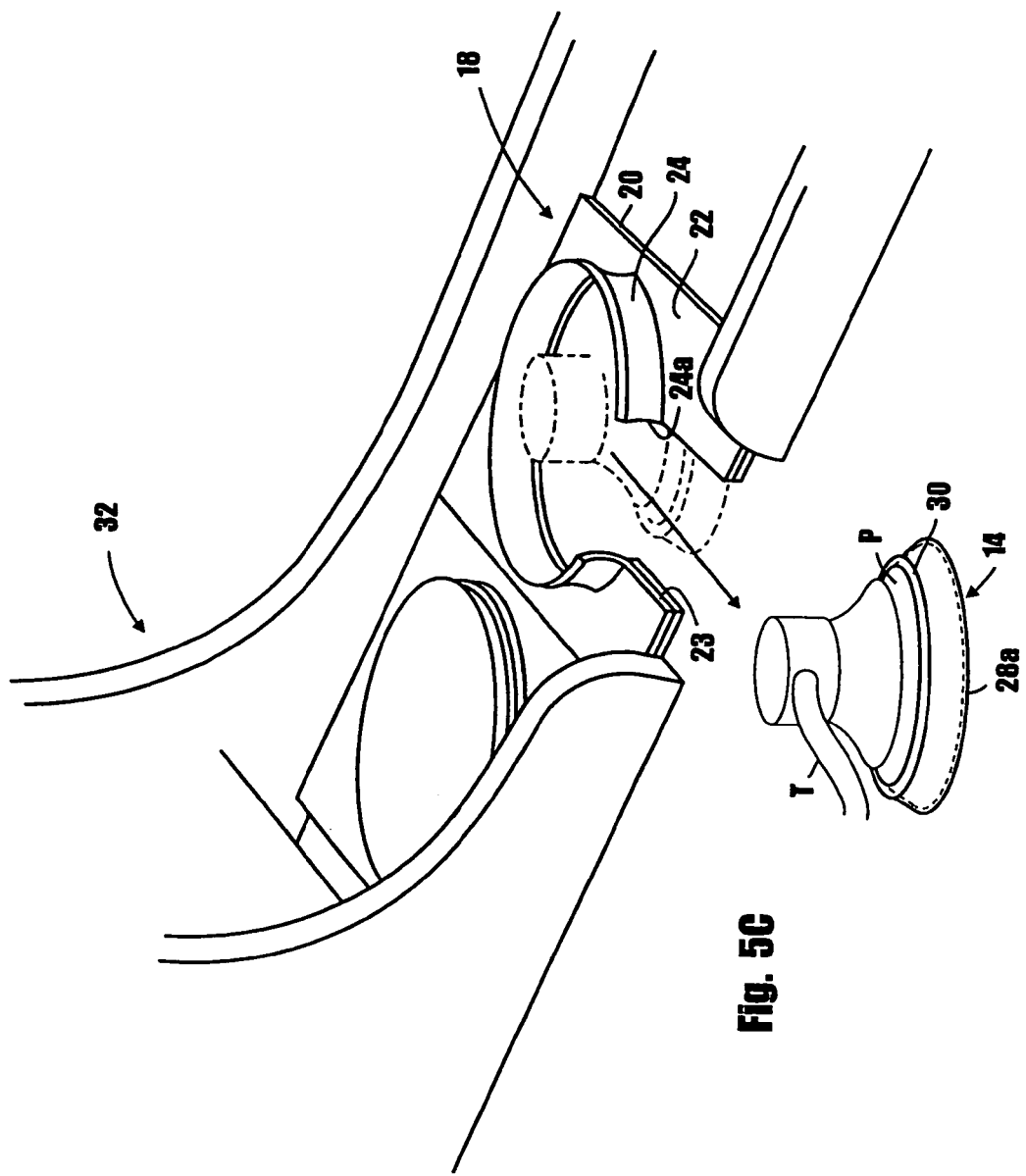

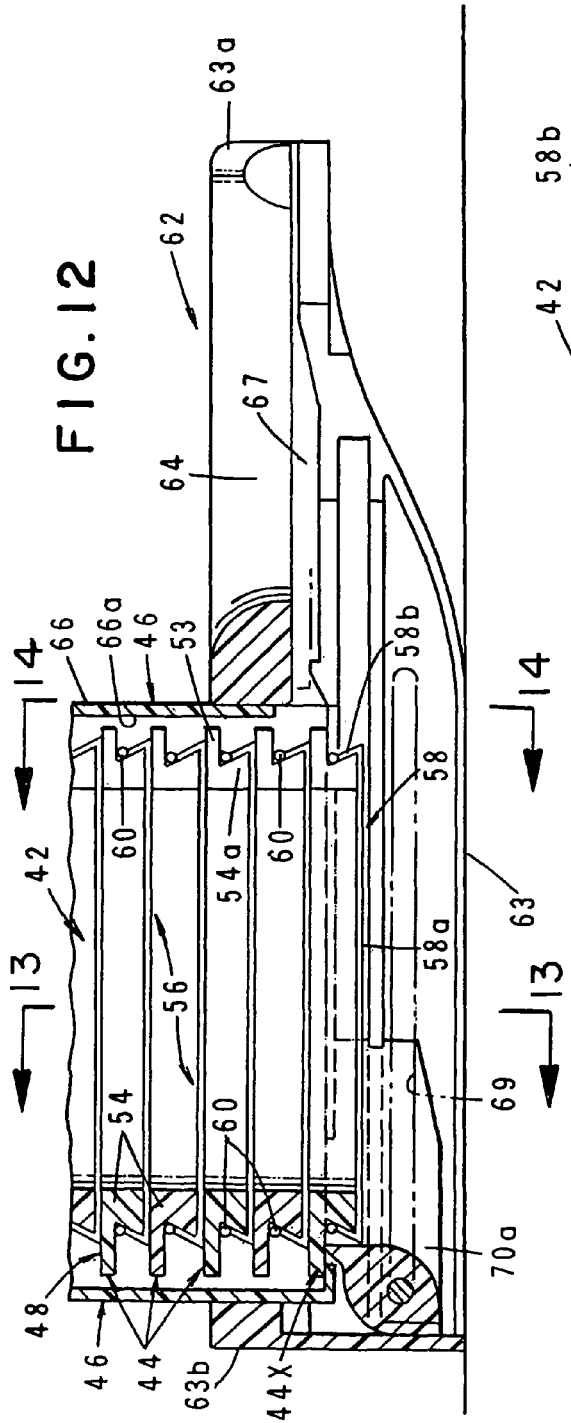
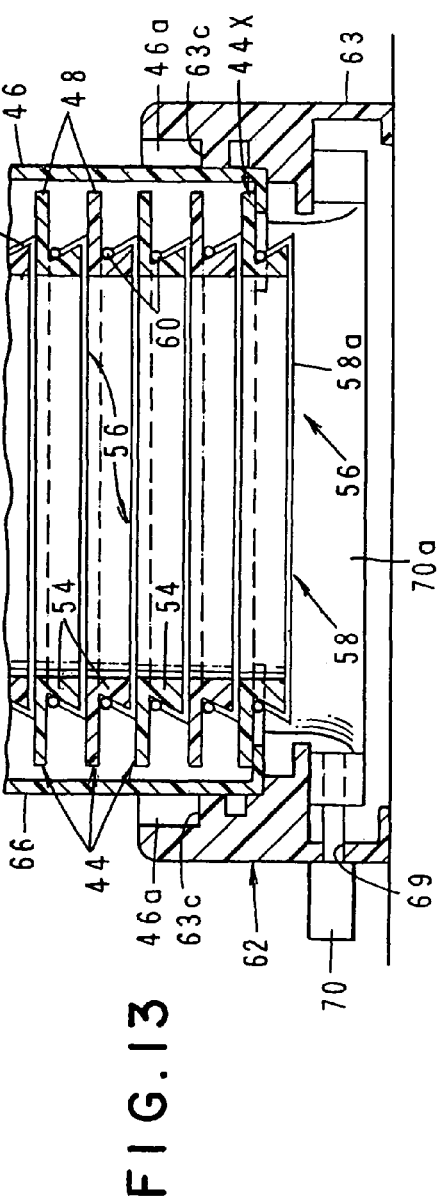
FIG.12
FIG.13

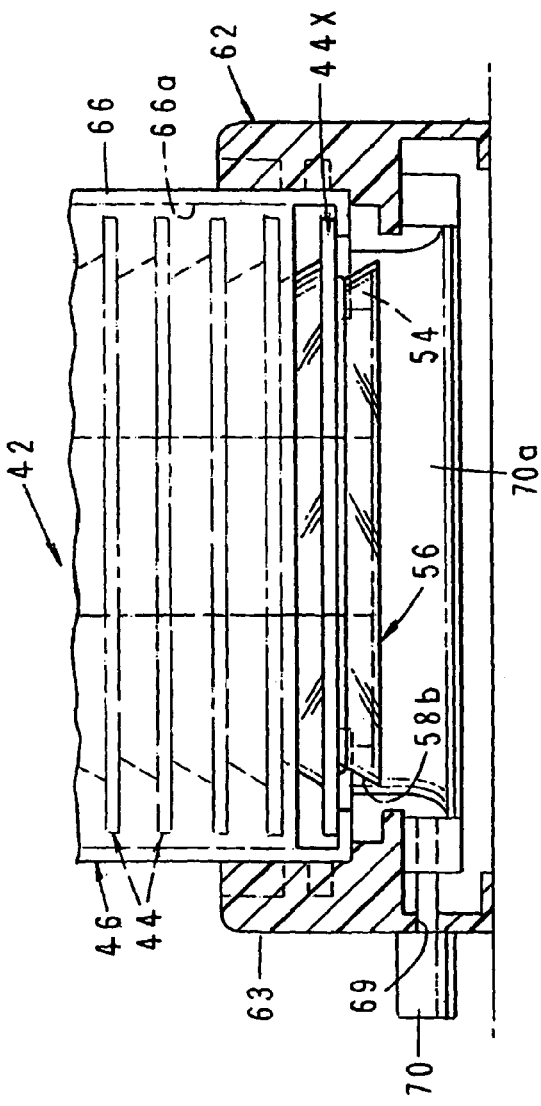
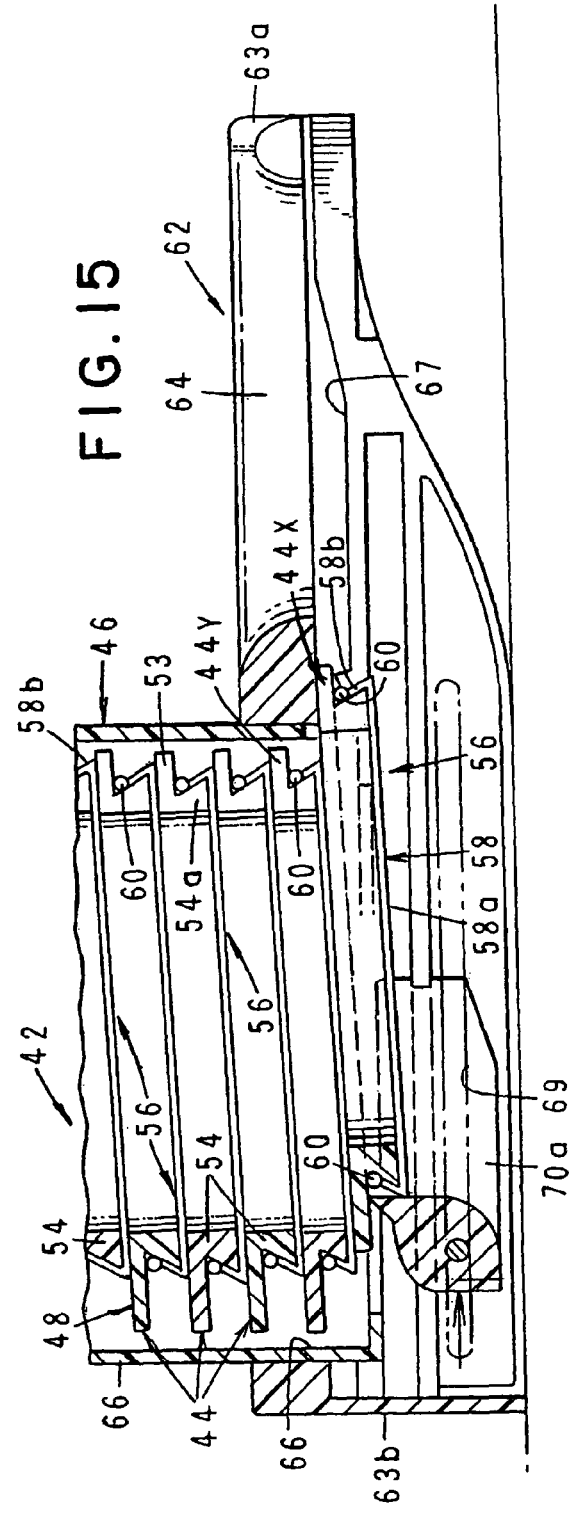

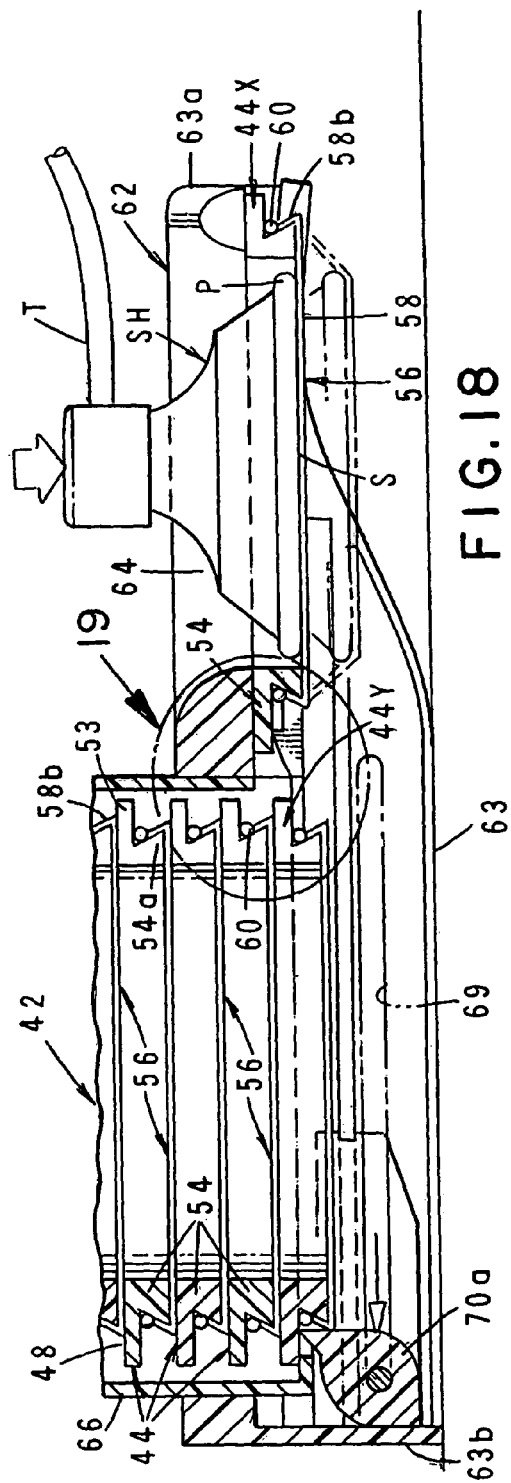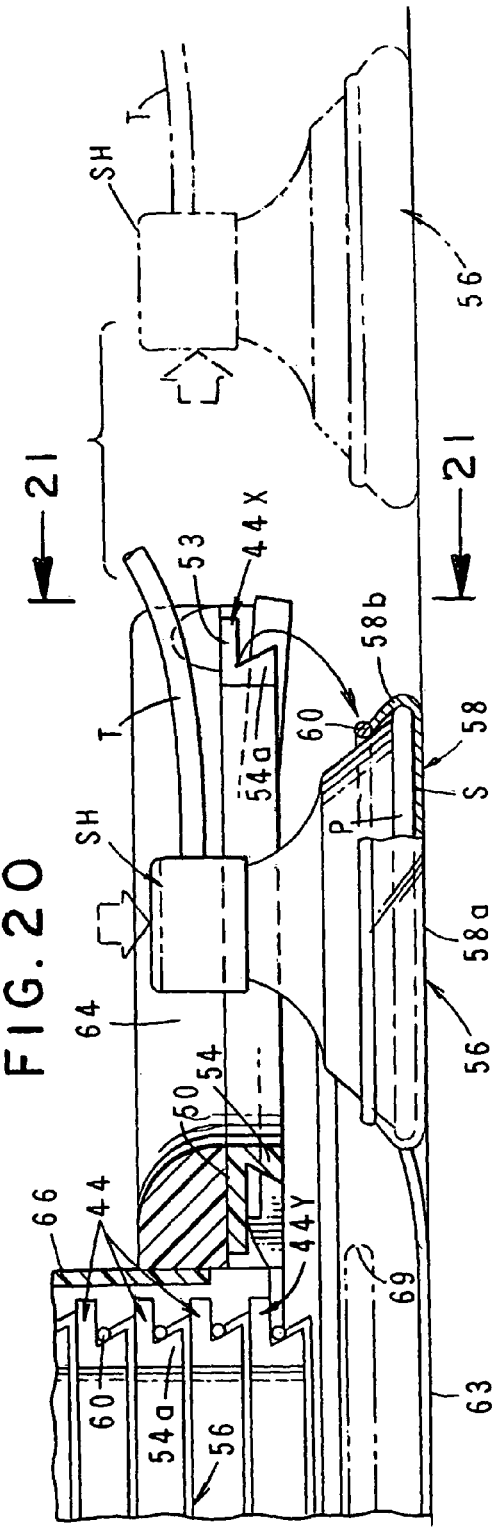

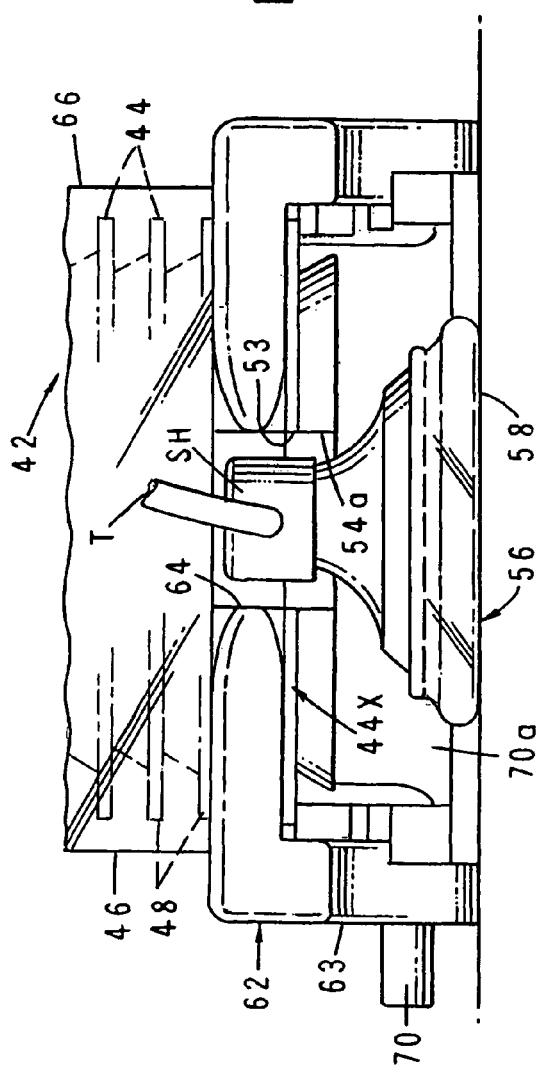
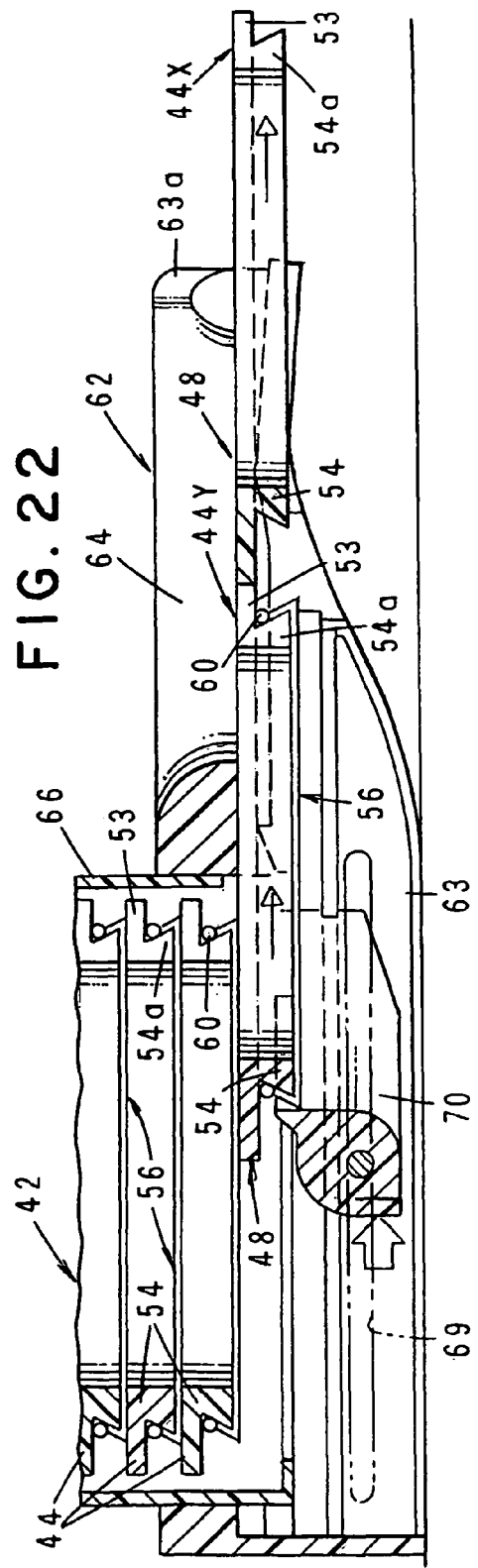

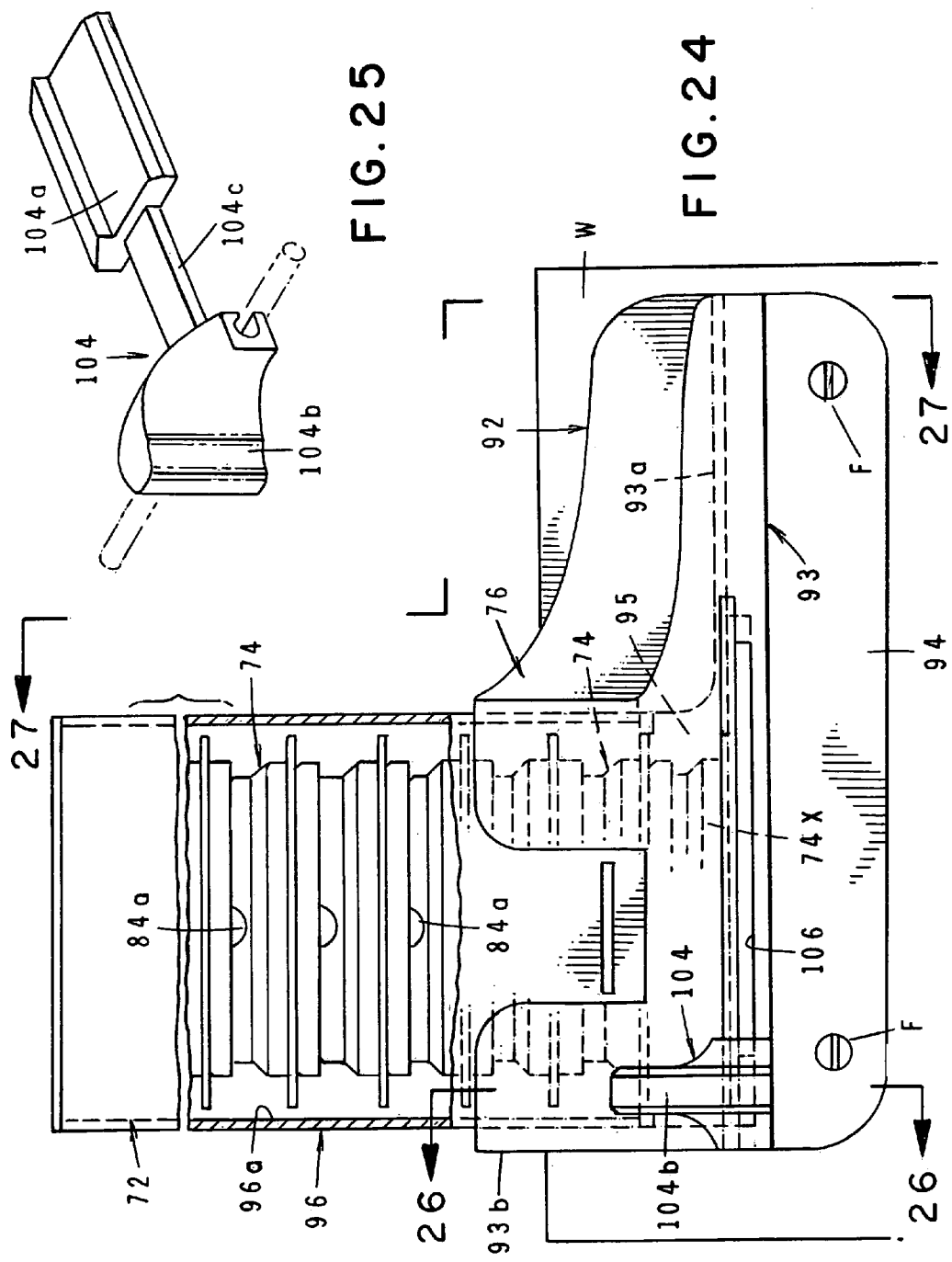

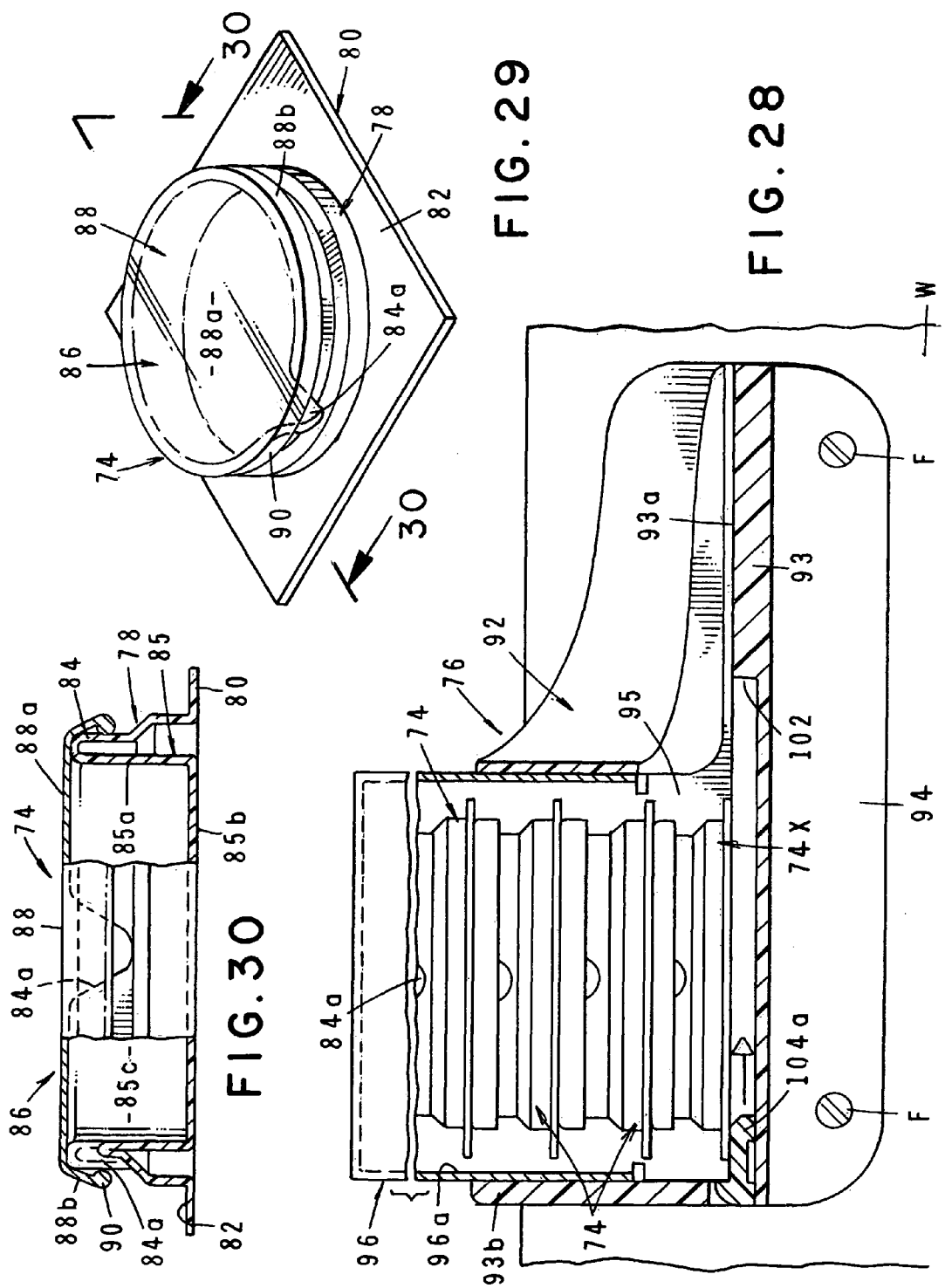

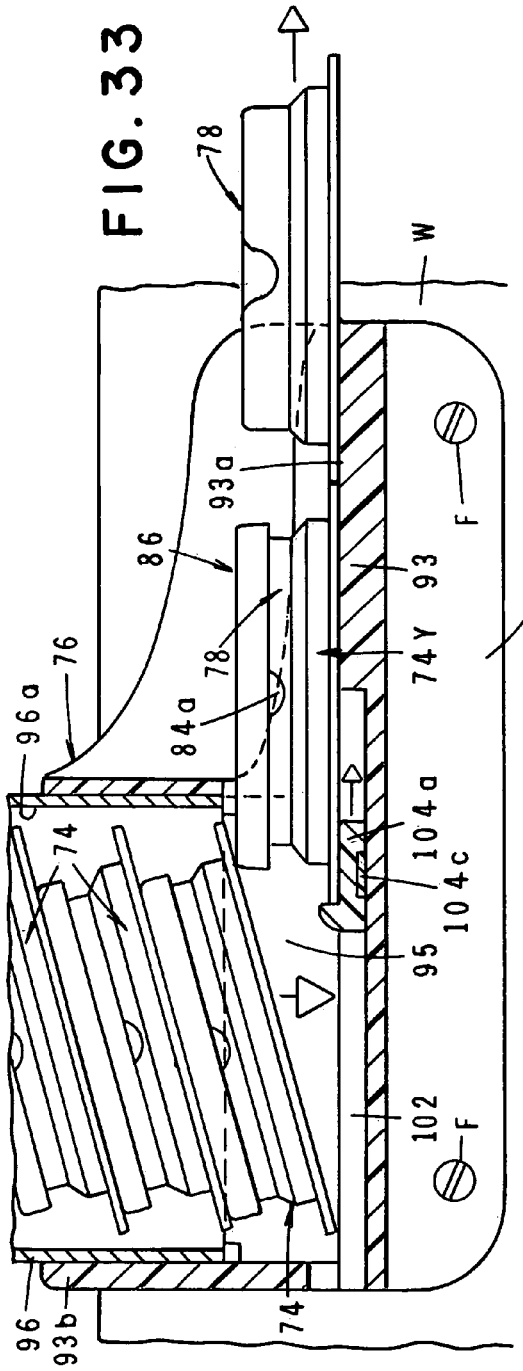
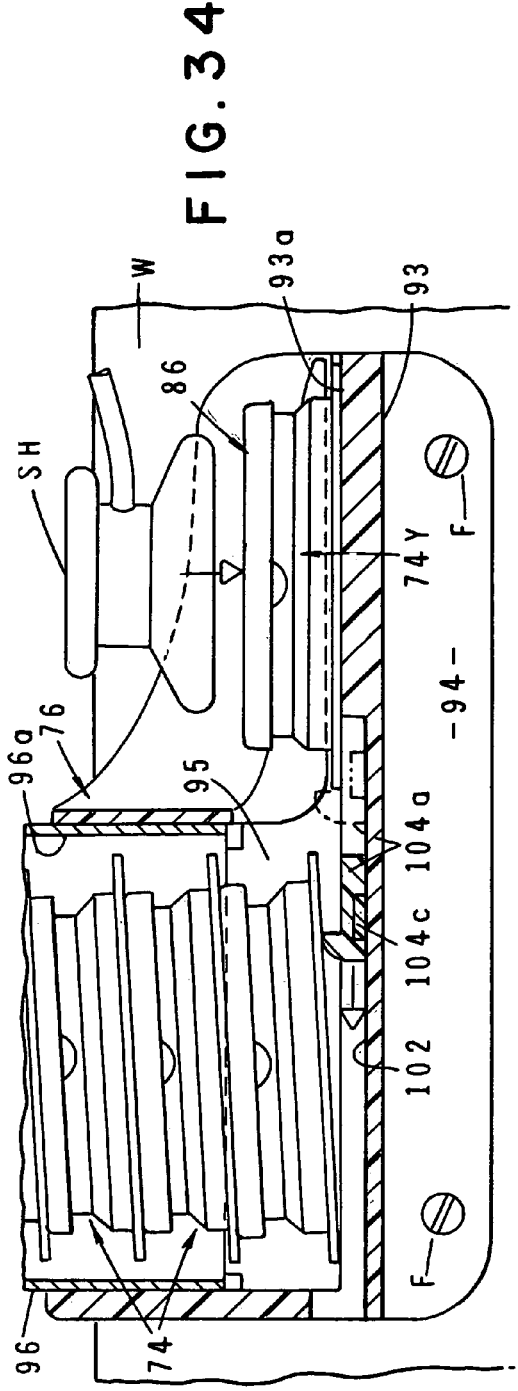
FIG.33
FIG.34

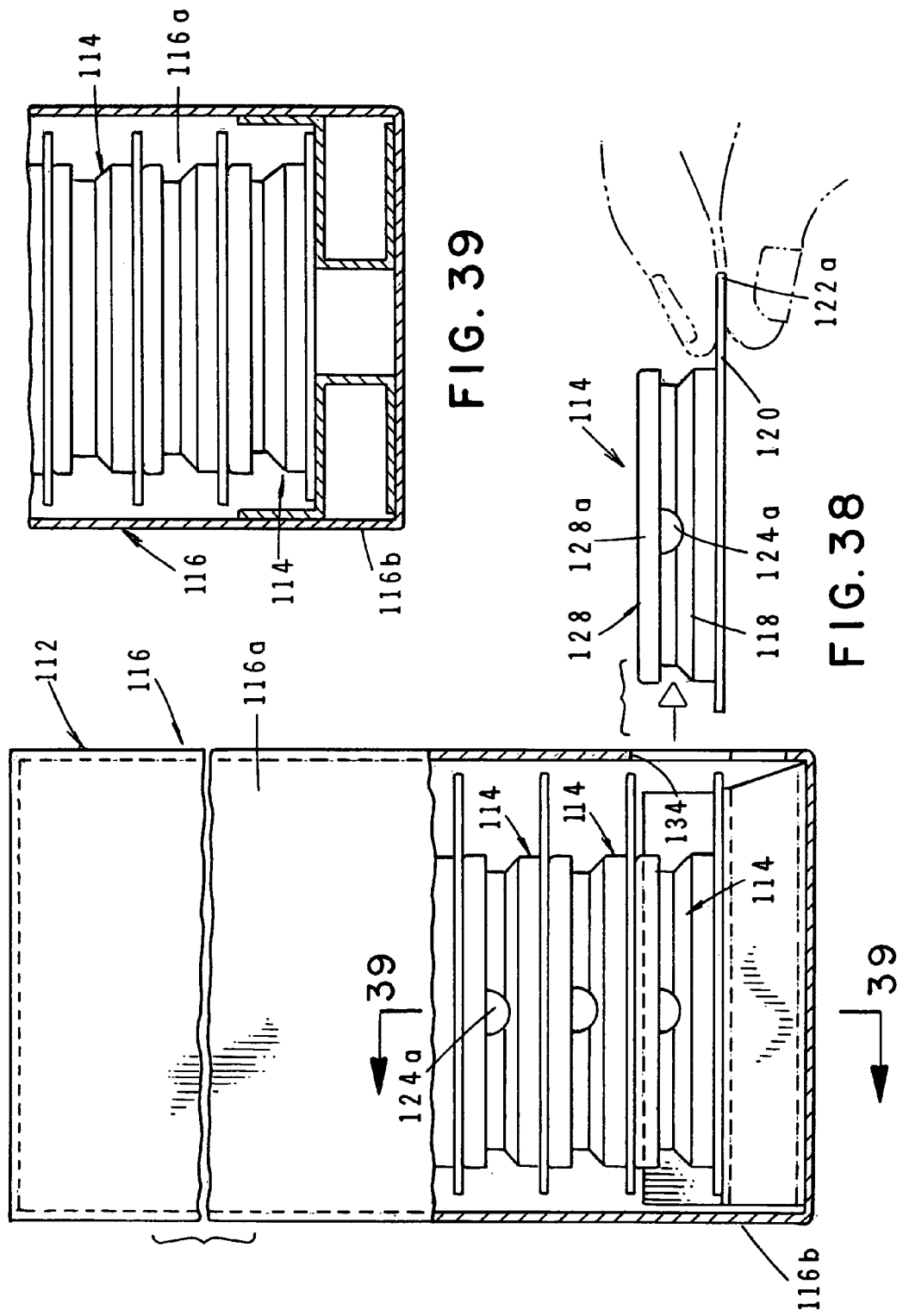

STETHOSCOPE COVER AND DISPENSER THEREFOR

CROSS-REFERENCE TO RELATED APPLICATIONS

This is a Continuation-In-Part application of co-pending U.S. application Ser. No. 12/590,299 filed Nov. 4, 2009 which is a Continuation Application of U.S. application Ser. No. 12/217,007 filed Jun. 30, 2008, now U.S. Pat. No. 7,614,478 which is a Continuation-In-Part of U.S. application Ser. No. 11/999,556 filed Dec. 5, 2007, now U.S. Pat. No. 7,469,769.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to medical devices. More particularly, the invention concerns a disposable cover for a stethoscope head and an apparatus for dispensing the disposable cover.

2. Description of Related Art Including Information Disclosed Under 37 CFR 1.97 and 1.98

A stethoscope is an acoustic medical device for auscultation, or listening, to internal sounds in a human or animal body. It is most often used to listen to heart sounds and breathing (breath sounds), though it is also used to listen to intestines and blood flow in arteries and veins. The stethoscope operates on the transmission of sound from the chest piece, via air-filled hollow tubes, to the listener's ears. The chest piece can be placed against the patient for sensing relatively high frequency sound via a diaphragm which is usually provided in the form of a plastic disc. If the diaphragm is placed on the patient, body sounds vibrate the diaphragm creating acoustic pressure waves which travel up the tubing to the listener's ears. In use, the stethoscope is typically applied to the skin of the neck, chest, or back portions of the patient and often becomes contaminated with skin bacteria and like contaminants that can undesirably be transmitted to the next patient unless the portions of the stethoscope that come in contact with a patient are sterilized after each use. The transmission of bacterial infections among patients, particularly in a hospital setting, has been aggravated by the development of antibiotic-resistant strains of staphylococcal infections. It is this problem that the apparatus of the present invention seeks to overcome by providing a novel stethoscope cover and a dispensing apparatus for quickly and easily dispensing the stethoscope cover.

A number of different types of stethoscope covers and apparatus for dispensing the covers have been suggested in the past. Exemplary of such prior art is the stethoscope cover and dispensing apparatus disclosed in U.S. Pat. No. 6,206,134 issued to Stark et al. The Stark et al. patent discloses a stethoscope head cover which overlies the diaphragm of the stethoscope and the surrounding rim thereof and is fabricated from a thin sheet of plastic with a discontinuous layer of peelable adhesive on one surface of the plastic. The discontinuous layer of adhesive is in a predetermined pattern and the pattern is selected so that air passageways are provided from the regions between the cover and the diaphragm and past the rim to regions external the stethoscope. The cover generally comprises a flat, thin plastic sheet with the discontinuous layer of a peelable adhesive applied to one surface of the sheet. The adhesive adheres to both the diaphragm and the rim of the stethoscope leaving the aforesaid air passages for eliminating trapped air pockets or bubbles between the diaphragm and the cover.

U.S. Pat. No. 6,019,187 issued to Appavu, discloses a disposable stethoscope cover diaphragm that is removably attached over the outer edge of a stethoscope high frequency pickup in order to isolate the pickup from pathogens contacted when the stethoscope is used to examine a person. The cover diaphragm can be used as the diaphragm of a stethoscope pickup and can be used with a diaphragm supplied with the stethoscope. After the cover diaphragm has been used it can be discarded and destroyed or, alternatively, can be cleaned for reuse.

U.S. Pat. No. 5,466,897 issued to Ross et al., discloses a dispenser for use in dispensing disposable stethoscope diaphragms for removable attachment to a stethoscope head, where the diaphragms are supplied in a stacked array in a tube. The diaphragms are dispensed by a plate slidably mounted on the base for movement between retracted and extended positions. A cradle formed in the plate receives a single diaphragm through the opening when the dispensing plate is in its retracted position. Movement of the dispensing plate from its retracted to extended position is effective to place a diaphragm in the plate cradle in a position that allows the diaphragm to be attached to a stethoscope head by pressing the stethoscope head against the diaphragm.

BRIEF SUMMARY OF THE INVENTION

By way of brief summary, one form of the present invention comprises a handheld cover dispensing unit that can be used to interconnect a disposable stethoscope cover with a conventional stethoscope head. The cover dispensing unit includes, in combination, a cover-positioning device and a disposable stethoscope cover for removable attachment to a stethoscope head. The cover-positioning device comprises a base having a planar portion and an upstanding rim connected to the planar portion, the upstanding rim defining an opening for receiving the stethoscope head therethrough. The disposable stethoscope cover comprises a thin, yieldably deformable membrane-like central portion having a peripheral portion and an elastomeric bead interconnected with the peripheral portion, the elastomeric bead being removably receivable over said upstanding rim of the cover-positioning device.

Another form of the present invention comprises a wall, or desktop mounted stethoscope head covering apparatus for dispensing a plurality of cover dispensing units of the character described in the preceding paragraph. This form of the invention includes a novel feed unit for sequentially dispensing the cover dispensing units. The feed unit includes a housing having a base having a forward portion and a rearward portion and an upstanding tower connected to the rearward portion of the base for holding a plurality of stacked cover dispensing units. An ejector slide is operably associated with the upstanding tower for moving a selected one of the cover dispensing units from the upstanding tower to a position over a generally key-hole shaped opening formed in said base of said feed unit so that the disposable cover can be conveniently interconnected with the stethoscope head.

With the forgoing in mind, it is an object of the invention to provide a novel handheld cover dispensing unit that can be used to quickly and easily interconnect a disposable, protective stethoscope cover with a stethoscope head.

Another object of the invention is to provide a cover-dispensing unit of the aforementioned character in which the protective stethoscope cover includes a thin, membrane-like central portion that is positioned in close protective engagement with the lower surface of the stethoscope head when the cover is interconnected with the stethoscope head.

Another object of the invention is to provide a protective stethoscope head cover of the character described in the preceding paragraph that can be quickly and easily removed from the stethoscope head following examination of the patient and then suitably disposed of so as to prevent skin bacteria and like contaminants, that may have contaminated the protective cover during patient examination, from undesirably being transmitted to the next patient.

Another object of the invention is to provide a hand-held dispensing unit of type described that is of simple compact construction and one that can be inexpensively manufactured in quantity.

Another object of the invention is to provide a novel wall or desk mounted feed unit that can be used to conveniently feed dispensing units of the character described from an upstanding tower containing a plurality of cover dispensing units and sequentially position them on a strategically designed base so that the protective cover of the dispensing unit can be removed from the cover positioning device and quickly and easily interconnected with a stethoscope head.

These and other objectives of the invention will be met by the novel apparatus of the invention, the character of which is described in the paragraphs that follow.

BRIEF DESCRIPTION OF SEVERAL VIEWS OF THE DRAWINGS

FIG. 3 is a generally perspective, exploded view of one form of the feed unit of the invention for sequentially dispensing the cover dispensing units.

FIG. 4 is a generally perspective view, similar to FIG. 3, illustrating the manner in which the cover dispensing units are sequentially dispensed from the tower of the feed unit.

FIG. 5 is a greatly enlarged, fragmentary, foreshortened, cross-sectional, side-elevational view illustrating the manner in which the cover dispensing units of the invention are stacked within the tower of the feed unit and are strategically positioned on the base of the feed unit for interconnection of the disposable cover with a stethoscope head of the general character illustrated in the phantom lines in FIG. 5.

FIG. 5A is a fragmentary view, similar to the right-hand portion of FIG. 5, illustrating the manner in which the stethoscope head, shown in phantom lines, is mated with the cover-positioning device.

FIG. 5B is a fragmentary view, similar to FIG. 5A, illustrating the disposable cover having been interconnected with the stethoscope head which is here shown in phantom lines.

FIG. 5C is a generally illustrative view showing removal from the feed unit of the assemblage made up of the stethoscope head and the protective cover.

FIG. 12 is an enlarged cross-sectional view taken along lines 12-12 of FIG. 6.

FIG. 13 is a cross-sectional view taken along lines 13-13 of FIG. 12.

FIG. 14 is a cross-sectional view taken along lines 14-14 of FIG. 12.

FIG. 15 is a cross-sectional view similar to FIG. 12, but showing one of the cover dispenser units of the invention in position to be dispensed from the feed unit of the apparatus.

FIG. 18 is a cross-sectional view similar to FIG. 16, showing the cover dispenser unit fully dispensed from the feed unit of the apparatus and showing the stethoscope in position to be mated with the cover dispensing unit.

FIG. 20 is a cross-sectional view similar to FIG. 18, showing the stethoscope fully mated with the cover portion of the cover dispensing unit and showing in phantom lines the covered stethoscope removed from the base assembly.

FIG. 21 is a view taken along lines 21-21 of FIG. 20.

FIG. 22 is a cross-sectional view similar to FIG. 20, showing another of the plurality of cover dispenser units of the invention in position to be dispensed from the feed unit of the apparatus in an engagement with the first fully dispensed cover dispenser unit so as to eject it from the base assembly.

FIG. 24 is a side view of the cover positioning device shown in FIG. 23, the view being partly broken away to show internal construction.

FIG. 25 is a generally perspective, fragmentary view illustrating the construction of the cover ejector assembly of this latest form of the device.

FIG. 28 is a cross-sectional view taken along lines 28-28 of FIG. 27.

FIG. 29 is a generally perspective view of one form of the disposable stethoscope head cover and supporting frame of the invention.

FIG. 30 is a cross-sectional view taken along lines 30-30 of FIG. 29.

FIG. 33 is a view similar to FIG. 28 illustrating the step of moving a second disposable stethoscope head cover and supporting frame in position to be interconnected with the stethoscope head.

FIG. 34 is a view similar to FIG. 31 illustrating the method of affixing the second disposable stethoscope head cover to the stethoscope head.

FIG. 38 is a generally illustrative view illustrating the method of removing a disposable stethoscope head cover from the dispensing unit of the invention so that the head cover can be positioned for interconnection with a stethoscope head.

FIG. 39 is a cross-sectional view taken along lines 39-39 of FIG. 38.

DETAILED DESCRIPTION OF THE INVENTION

Figure 1:
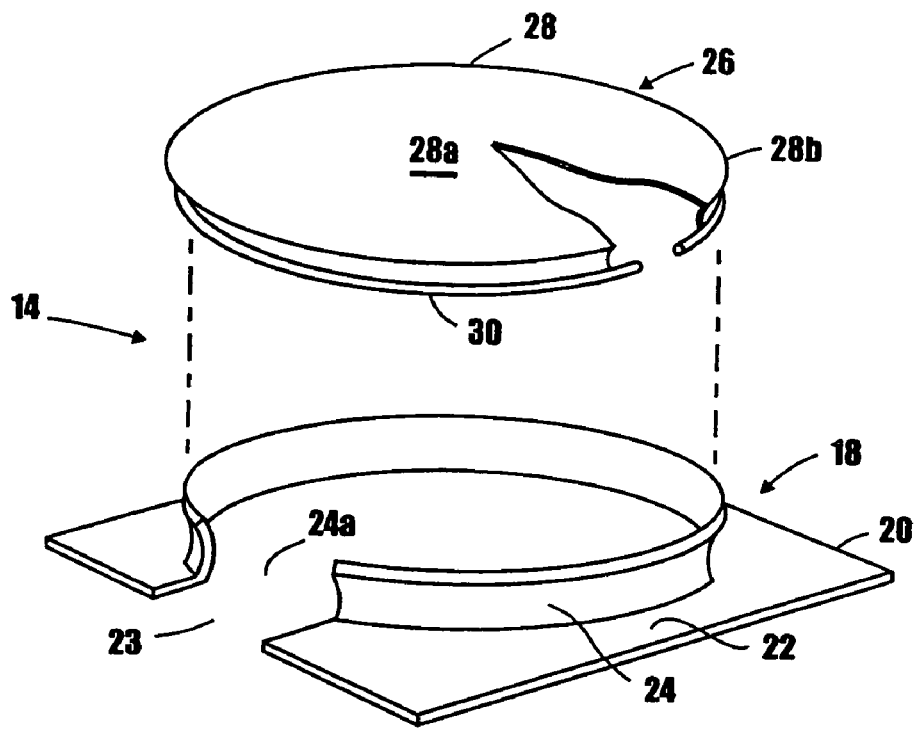
FIG. 1 is a generally perspective, exploded view of one form of the cover position devices of the invention for positioning a disposable stethoscope head cover in the manner such that the cover can be conveniently interconnected with a stethoscope head.

Referring to the drawings and particularly to FIGS. 3 and 4, one form of the stethoscope head covering apparatus of the present invention is there shown and generally designated by the numeral 12. Apparatus 12 here comprises a plurality of cover dispensing units 14 of the character illustrated in FIG. 2 of the drawings and a feed unit 16 of the character shown in FIGS. 3 and 4 of the drawings. In a manner presently to be described, feed unit 16 functions to sequentially dispense the plurality of cover dispensing units 14. However, it is to be understood that, as previously described, the cover dispensing units 14 can be packaged and distributed as individual handheld units that can be used by the physician to interconnect the protective cover with the stethoscope head.

Figure 2:
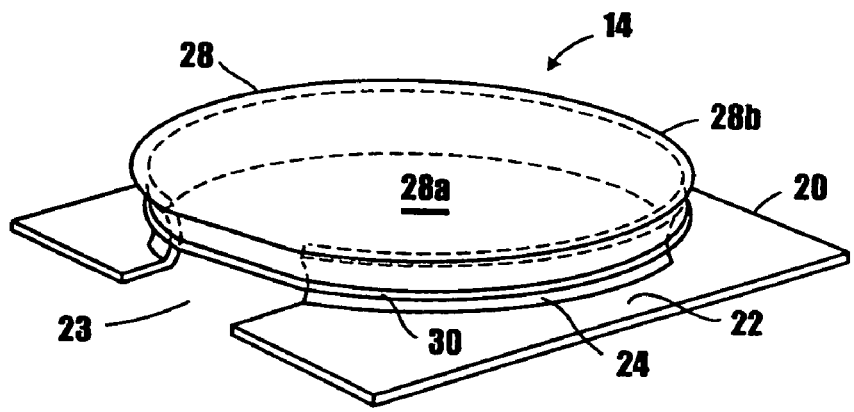
FIG. 2 is a generally perspective view, similar to FIG. 1, showing the disposable stethoscope head cover interconnected with the cover-positioning device to form the cover dispenser unit of the invention.

As best seen in FIGS. 1 and 2 of the drawings, each cover dispensing unit 14 comprises a positioning device 18 that includes a base 20 having a generally planar portion 22 and an upstanding rim 24 that is connected to portion 22 in the manner shown in FIG. 1. For a purpose presently to be described, generally planar portion 22 of the base is provided with an open segment 23. Similarly, upstanding rim 24 is provided with an open segment 24a that is disposed in alignment with open segment 23 of the planar portion of the base.

Connected to each of the cover-positioning devices 18 to form a dispensing unit 14 (see FIG. 2) is a cover assembly 26 that comprises a uniquely constructed disposable cover 28. As best seen in FIG. 1, disposable cover 28 has a thin, yieldably deformable, membrane-like central portion 28a and a peripheral portion 28b. Connected to peripheral portion 28b is an elastomeric bead 30 that is removably receivable over the upstanding rim 24 of the base 20 in the manner shown in FIG. 2 of the drawings.

Considering once again the dispenser unit 16 of the apparatus of the invention, as illustrated in FIGS. 3 and 4 of the drawings, dispenser unit 16 here comprises a base 32 having a forward portion 32a and a rearward portion 32b. As indicated in FIG. 3 of the drawings, forward portion 32a is provided with a generally key-hole-shaped opening 34, the purpose of which will presently be described.

Connected to the rearward portion 32b of base 32 is an upstanding dispensing tower 36 having an interior chamber 36a (FIG. 5) that, in the manner shown in FIG. 5, functions to hold a plurality of stacked cover dispensing units 14. For a purpose presently to be described, the chamber is provided with a slot 36a that is formed proximate the rearward portion 32b of the base (see FIG. 5). Slidably receivable within slot 36a for movement between a first retracted position and a second dispensing position is an ejector slide 38. When the selector slide has been moved from its first retracted position to its second dispensing position, a selected one of the cover dispensing units 14, such as the device identified in FIGS. 3 and 4 by the numeral 14x, has been moved along the base 32 from the inward position shown in FIG. 3 into the outward position shown in FIGS. 4 and 5 wherein it resides over the generally key-hole-shaped opening 34.

With the cover dispensing units designated as 14x in position over the generally key-hole-shaped opening 34 (FIG. 5), the disposable cover assembly 26 can be interconnected with the stethoscope head in the manner illustrated in FIGS. 5, 5A and 5B of the drawings. More particularly, in order to interconnect the disposable cover with the stethoscope head, the stethoscope head is moved in the direction of the arrow 41 of FIG. 5A from the position shown in the phantom lines in FIG. 5 into the downward position shown by the phantom lines in FIG. 5A, where it is in engagement with the yieldably deformable central portion 28a of the cover. A continued downward movement of the stethoscope head in the direction of the arrow 41 of FIG. 5A will cause a deformation of the central portion of the cover in the manner shown in FIG. 5A. A further downward movement of the stethoscope head to the position shown in FIG. 5B will cause it to move through the generally key-hole-shaped opening 34 (see FIG. 3) and into the position shown in FIG. 5B of the drawings. As the stethoscope head moves downwardly through the keyhole shaped opening, the air-filled hollow tubes "T" of the stethoscope will pass through the segmented openings 23 and 24a formed in the base 20 and in the upstanding rim 24, respectively. As the stethoscope head moves downwardly, the elastomeric bead 30 will release from the rim portion of the base and, in the manner illustrated by the arrows 43 and FIG. 5A, will move into engagement with the peripheral portion "P" of the stethoscope head, thereby removably securing the cover 28 to the stethoscope head and moving the flexible central membrane portion 28a of the cover into close engagement with the lower surface "S" of the stethoscope head. Once the cover is in position over the stethoscope head, the assemblage thus formed can be removed from the apparatus 12 in the manner illustrated in FIG. 5C. Following the examination of the patient, the cover assembly 26 can be conveniently removed from the stethoscope head and discarded into a suitable contaminated waste receptacle.

Turning next to FIGS. 6 through 10, an alternate form of the stethoscope head covering apparatus of the present invention is there shown and generally designated by the numeral 42. Apparatus 42, which is similar in many respects to the embodiment shown in FIGS. 1 through 5, here comprises a plurality of cover dispensing units 44 of the character illustrated in FIGS. 8 and 9 of the drawings and a feed unit 46 of the character shown in FIGS. 6 and 7 of the drawings. In a manner presently to be described, feed unit 46 functions to sequentially dispense the plurality of cover dispensing units 44. However, it is to be understood that, as previously described, the cover dispensing units 44 can be packaged and distributed as individual handheld units that can be used by the physician to interconnect the protective cover with the stethoscope head.

Figure 8:
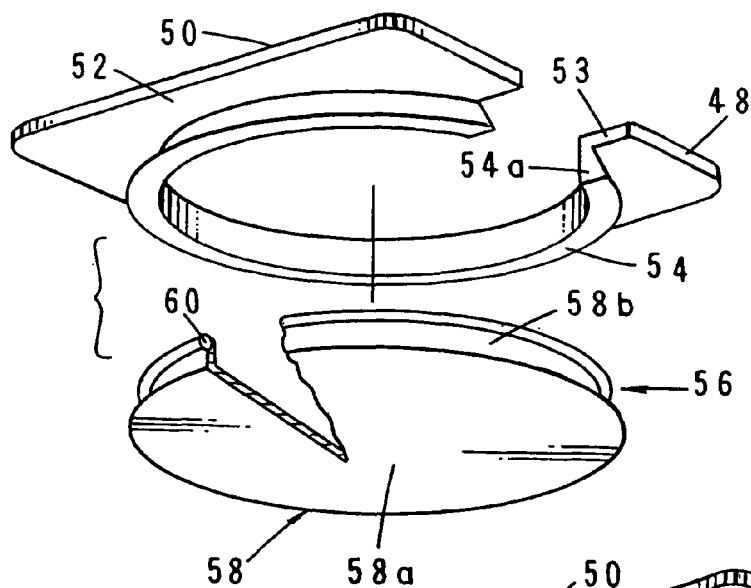
FIG. 8 is a generally perspective, exploded view of one form of the cover position devices of the invention for positioning a disposable stethoscope head cover in the manner such that the cover can be conveniently interconnected with a stethoscope head.
Figure 9:
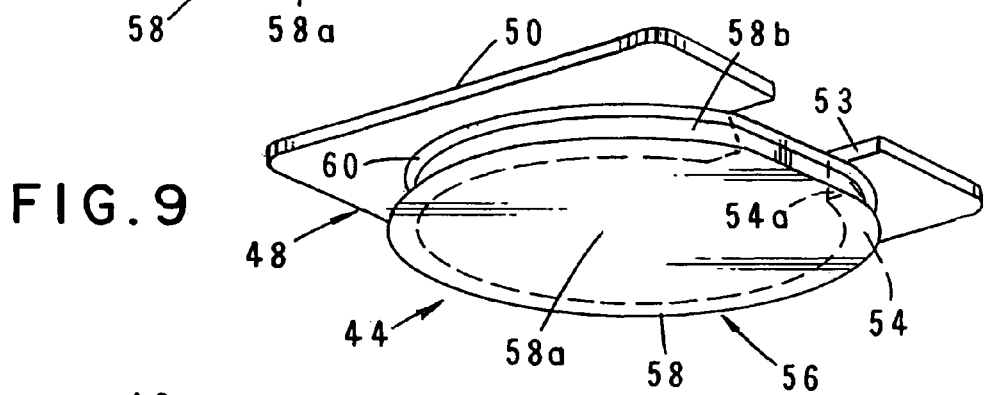
FIG. 9 is a generally perspective bottom view, similar to FIG. 8, showing the disposable stethoscope head cover interconnected with the cover-positioning device to form the cover dispenser unit of the invention.
Figure 10:
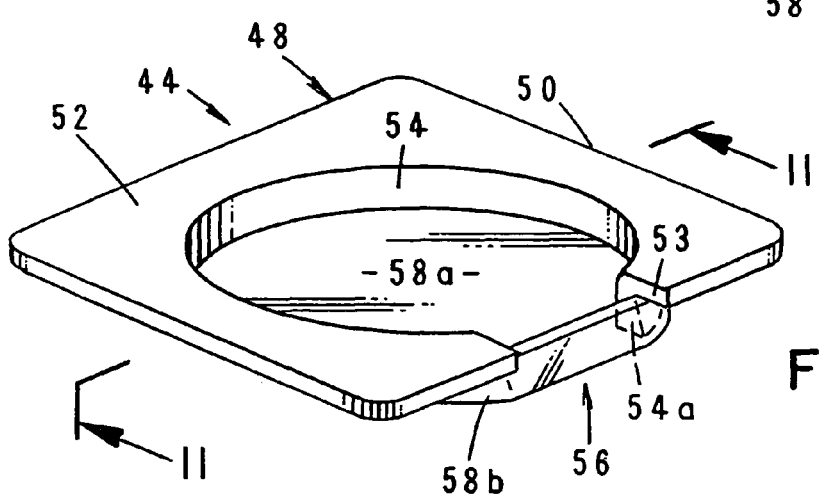
FIG. 10 is a generally perspective top view, similar to FIG. 9, showing the disposable stethoscope head cover interconnected with the cover-positioning device.
Figure 17:
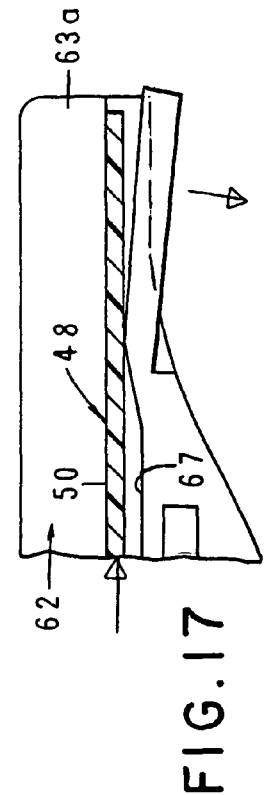
FIG. 17 is a greatly enlarged fragmentary cross-sectional view of the area designated in FIG. 16 as "17".

As best seen in FIGS. 8 through 10 of the drawings, each cover dispensing unit 44 comprises a positioning device 48 that includes a positioning base 50 having a generally planar portion 52 (FIG. 8) and a rim 54 that is connected to positioning base 50 in the manner shown in FIG. 10. For a purpose presently to be described, generally planar portion 52 of the positioning base is provided with an open segment 53. Similarly, upstanding rim 54 is provided with an open segment 54a that is disposed in alignment with open segment 53 of the positioning base.

Figure 11:
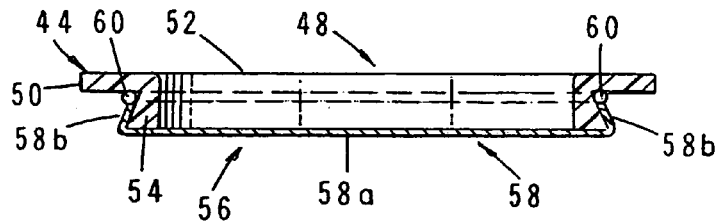
FIG. 11 is a cross-sectional view taken along lines 11-11 of FIG. 10.

Connected to each of the cover-positioning devices 48 to form a dispensing unit 44 (see FIG. 8), is a cover assembly 56 that comprises a uniquely constructed disposable cover 58. As best seen in FIG. 9 disposable cover 58 has a thin, yieldably deformable, membrane-like central portion 58a and a peripheral portion 58b. Connected to peripheral portion 58b is an elastomeric bead 60 that is removably receivable over rim 54 of the base 50 in the manner shown in FIGS. 9 and 11 of the drawings.

Figure 6:
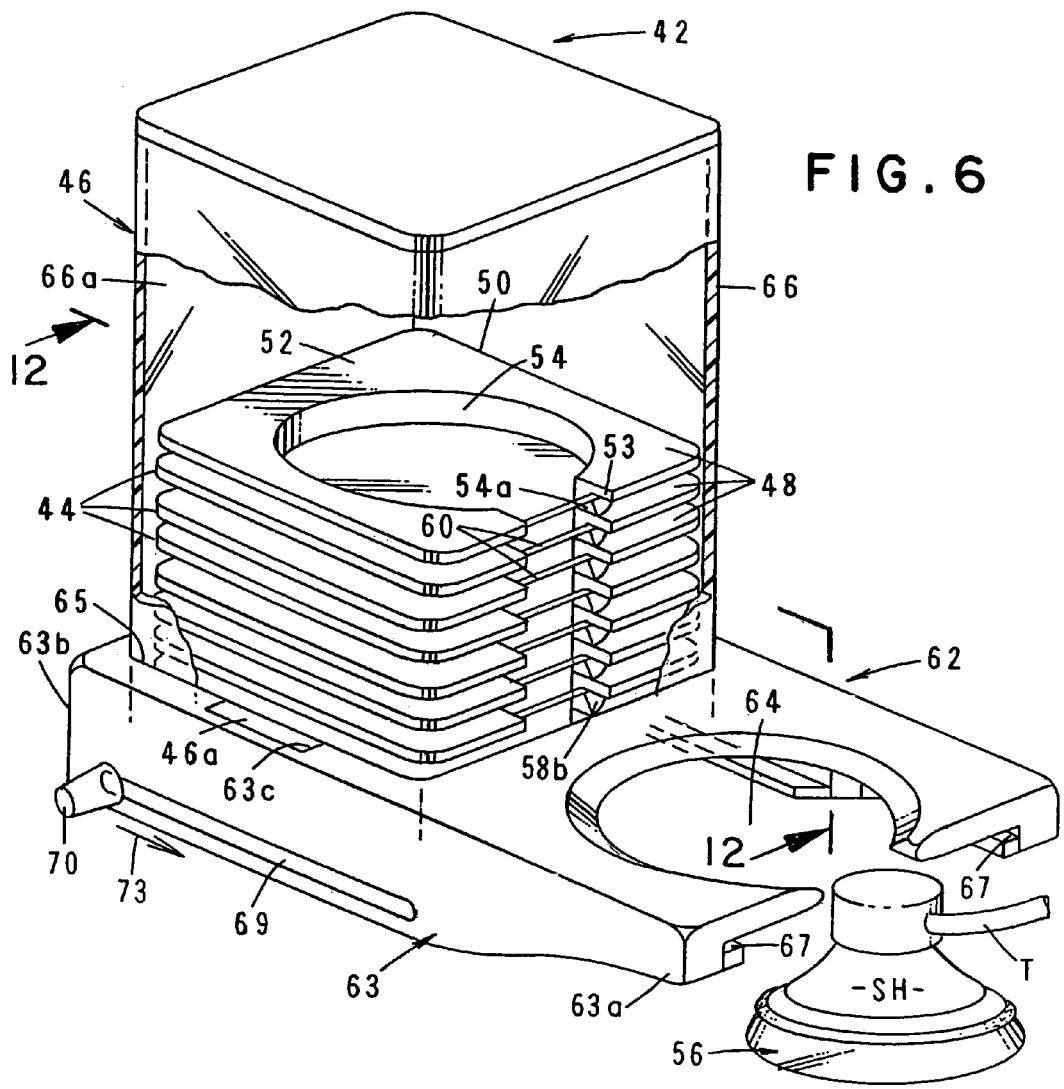
FIG. 6 is a generally perspective view of an alternate form of the cover position devices of the invention for positioning a disposable stethoscope head cover in the manner such that the cover can be conveniently interconnected with a stethoscope head.
Figure 7:
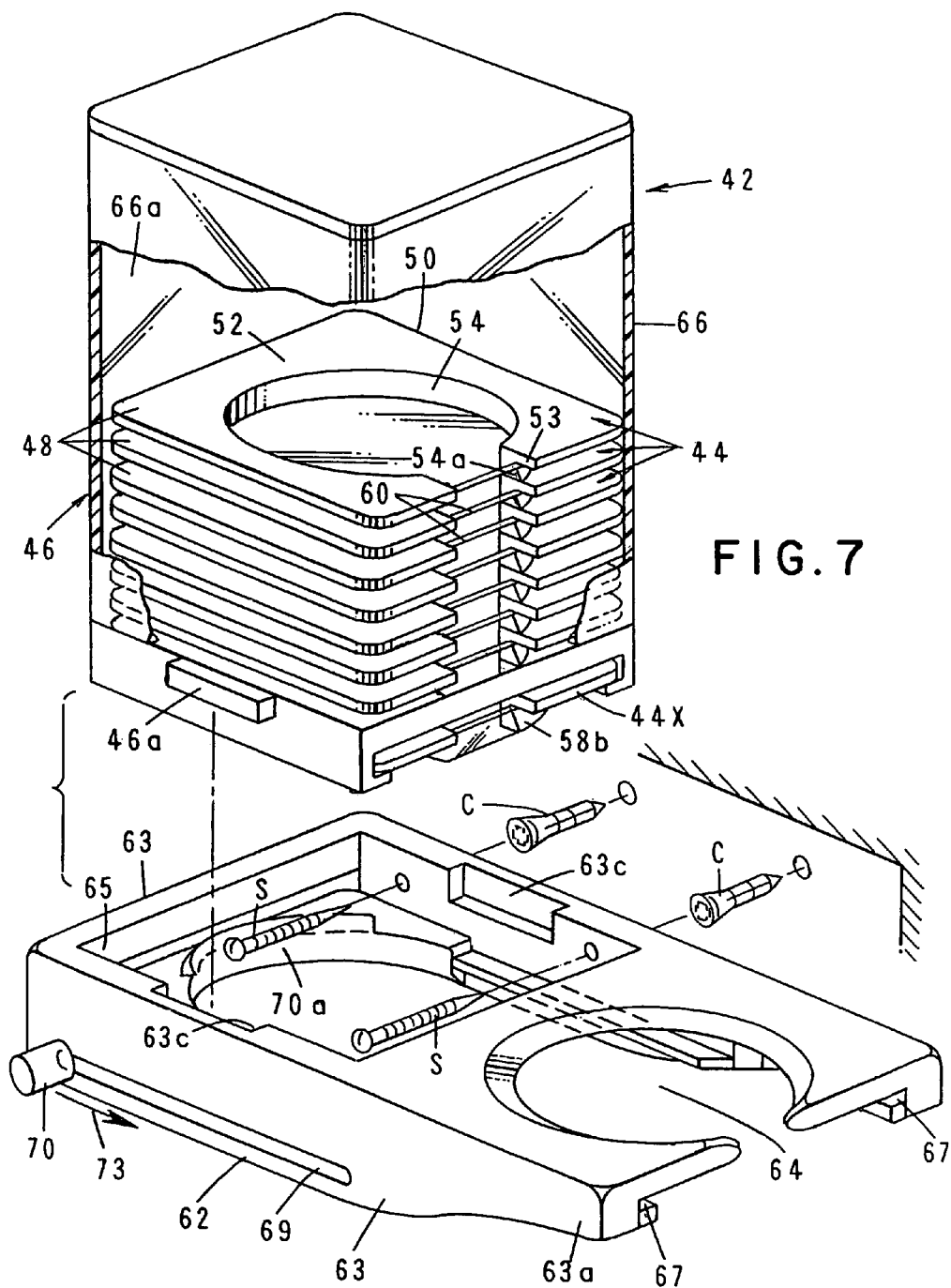
FIG. 7 is a generally perspective view, similar to FIG. 6, but showing the feed unit of the apparatus for dispensing the cover-positioning devices exploded from the base assembly of the apparatus.

Considering once again the dispenser unit 46 of the apparatus of the invention, as illustrated in FIGS. 6 and 7 of the drawings, dispenser unit 46 here comprises a base assembly 62 that includes a base 63 having a forward portion 63a and a rearward portion 63b. A novel feature is illustrated in FIG. 7 where the base assembly 62 can be attached to a vertical wall by fasteners "F" and anchors "C". As indicated in FIG. 7 of the drawings, rearward portion 63b is provided with a feed unit receiving chamber 65, while forward portion 63a is provided with a generally key-hole-shaped opening 64, the purpose of which will presently be described.

Receivable within feed unit receiving chamber 65 is the previously identified feed unit 46 that includes an upstanding dispensing tower 66 having an interior chamber 66a (FIG. 7) that, in the manner shown in FIGS. 6 and 7, functions to hold the plurality of stacked cover dispensing units 44. As best seen in FIG. 7, to insure correct alignment of the feed unit 46, base 63 of base assembly 62 is provided with a pair of index slots 63c that closely receive a pair of indexing protuberances 46a formed on feed unit 46 (FIG. 6). For a purpose presently to be described, base 63 is also provided with a guide channel 67 that communicates with feed unit receiving chamber 65 (FIG. 7) and functions to slidably receive a selected one of the stacked cover dispensing units 44 for movement between a first retracted position and a second dispensing position.

Figure 16:
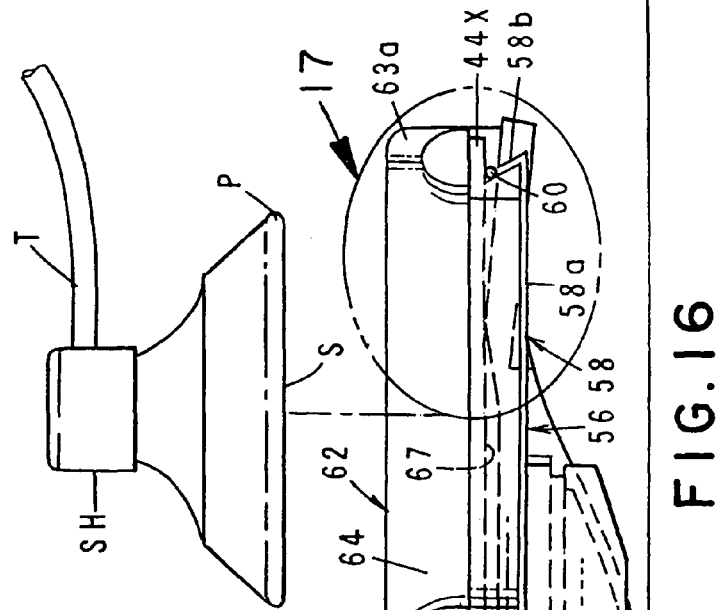
FIG. 16 is a fragmentary cross-sectional view similar to FIG. 15, but showing the cover dispenser unit fully dispensed from the feed unit of the apparatus.

Base 63 is also provided with a longitudinal slot 69 that slidably receives the pusher segment 70a of a finger engaging dispenser knob 70 that is adapted for movement in the direction of the arrow 73 of FIG. 7, between a first retracted position and a second dispensing position. When the finger engaging dispenser knob 70 is moved from its first retracted position to its second dispensing position, the pusher segment 70a of a finger engaging dispenser knob engages a selected one of the cover dispensing units 44, such as the device identified in FIG. 16 by the numeral 44x, and is moved within guide channel 67 from the inward position shown in FIG. 16 to an outward position wherein it resides beneath the generally key-hole-shaped opening 64.

With the cover dispensing unit designated as 44x, is in position beneath the generally key-hole-shaped opening 64, the disposable cover assembly 56 can be interconnected with the stethoscope head in the manner illustrated in FIGS. 18 and 20 of the drawings. More particularly, in order to interconnect the disposable cover with the stethoscope head, the stethoscope head is moved from the position shown in FIG. 18 into the downward position shown in FIG. 20 where it is in engagement with the yieldably deformable central portion 58a of the cover. A continued downward movement of the stethoscope head to the position shown in FIG. 20 will cause it to move through the generally key-hole-shaped opening 64 and into the stethoscope covered position shown in FIGS. 20 and 21 of the drawings. As a stethoscope head moves downwardly through the keyhole shaped opening, the air-filled hollow tubes "T" of the stethoscope will pass through the segmented openings 53 and 54a formed in the base 50 and in the rim 54, respectively. Importantly, as the stethoscope head moves downwardly into the position shown in FIGS. 20 and 21 of the drawings, the elastomeric bead 60 will release from the rim portion of the base and will move into engagement with the peripheral portion "P" of the stethoscope head, thereby removably securing the cover 56 to the stethoscope head. In this position, the flexible central membrane portion 58a of the cover resides in close engagement with the lower surface "S" of the stethoscope head. Once the cover is in position over the stethoscope head, the assemblage thus formed can be removed from the apparatus in the manner illustrated by the phantom lines in FIG. 20. Following the examination of the patient, the cover assembly 56 can be conveniently removed from the stethoscope head and discarded into a suitable contaminated waste receptacle.

In using this apparatus of the invention, the feed unit 46 is first mated with the base assembly 62 in the manner shown in FIG. 12 of the drawings. This done, movement of the finger engaging dispenser knob 70 from its first retracted position into the position shown in FIG. 15 of the drawings will cause the pusher segment 70a of the finger engaging dispenser knob to engage the cover dispensing unit 44x and move it forwardly within guide channel 67. Further movement of the finger engaging dispenser knob will cause the cover dispensing unit 44x to move into the second outward position wherein it resides beneath the generally key-hole-shaped opening 64 (see FIGS. 16 and 18). At the same time, the cover dispensing unit identified in FIGS. 16 and 18 by the numeral 44y will drop downwardly into the position earlier occupied by cover dispensing unit 44x.

Figure 19:
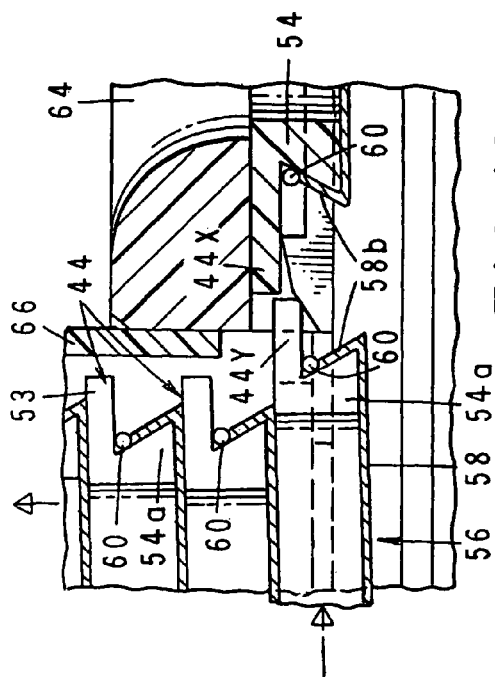
FIG. 19 is a greatly enlarged fragmentary cross-sectional view of the area designated in FIG. 18 as "19".

With the cover dispensing unit designated as 44x thusly positioned beneath the generally key-hole-shaped opening 64, the stethoscope head is moved from the position shown in FIG. 18 into the downward position shown in FIG. 19 where it is in engagement with the yieldably deformable central portion 58a of the cover. A continued downward movement of the stethoscope head to the position shown in FIG. 20 will cause it to move through the generally key-hole-shaped opening 64 and into the stethoscope covered position shown in FIGS. 20 and 21 of the drawings. As the stethoscope head moves downwardly through the keyhole shaped opening, the elastomeric bead 60 will release from the rim portion of the base and move into engagement with the peripheral portion "P" of the stethoscope head, thereby removably securing the cover 56 to the stethoscope head. Once the cover is in position over the stethoscope head, the assemblage thus formed can be removed from the apparatus in the manner illustrated by the phantom lines in FIG. 20. Following the examination of the patient, the cover assembly 56 can be conveniently removed from the stethoscope head and discarded into a suitable contaminated waste receptacle.

To cover the stethoscope head with a fresh cover assembly 56, finger engaging dispenser knob 70 is returned to its first starting position wherein the pusher segment 70a is in engagement with the cover dispensing unit 44y. Forward movement of the finger engaging dispensing knob 70 from this starting position will cause the pusher segment 70a of the finger engaging dispenser knob to move the cover dispensing unit 44y forwardly within guide channel 67 into the second outward position wherein it resides beneath the generally key-hole-shaped opening 64 (see FIGS. 16 and 18). At the same time, cover dispensing unit 44y will urge cover dispensing unit 44x outwardly of the base assembly. With a cover dispensing unit 44y disposed beneath the keyhole shaped opening 64, the fresh cover assembly 56 of cover dispensing unit 44y can be removably affixed to the stethoscope head in the manner previously described.

Turning next to FIGS. 23 through 35, still another form of the stethoscope head covering apparatus of the present invention is there shown and generally designated by the numeral 72. Apparatus 72, which is similar in many respects to the embodiment shown in FIGS. 6 through 22, here comprises a plurality of cover dispensing units 74 of the character illustrated in FIGS. 29 and 30 of the drawings and a feed unit 76 of the character shown in FIGS. 23 and 24 of the drawings. In a manner presently to be described, feed unit 76 functions to sequentially dispense the plurality of cover dispensing units 74.

As best seen in FIGS. 29 through 30 of the drawings, each cover dispensing unit 74 comprises a supporting frame 78 that includes a base 80 having a generally planar portion 82 (FIG. 29) and a rim 84 that is connected to positioning base 80 in the manner shown in FIGS. 29 and 30. For a purpose presently to be described, rim 84 is provided with a generally U-shaped opening 84a. Rim 84 is also connected to a chamber defining structure 85 that includes an upstanding side wall 85a and a base wall 85b that cooperates with the side wall to define a stethoscope head receiving chamber 85c (FIG. 30).

Figure 23:
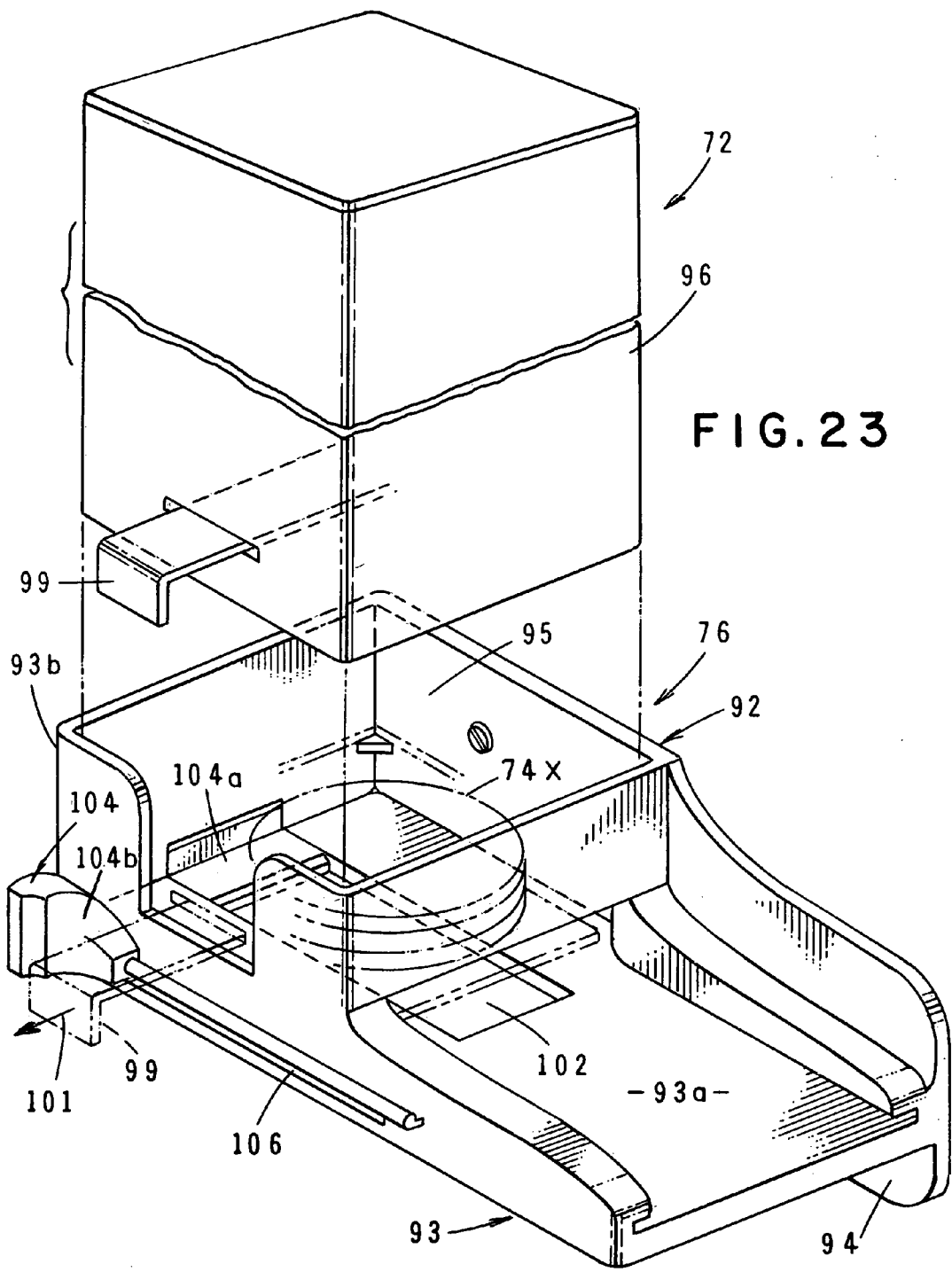
FIG. 23 is a generally perspective foreshortened view of still another form of the cover positioning devices of the invention for positioning a disposable stethoscope head cover in the manner such that the cover can be conveniently interconnected with a stethoscope head.
Figure 26:
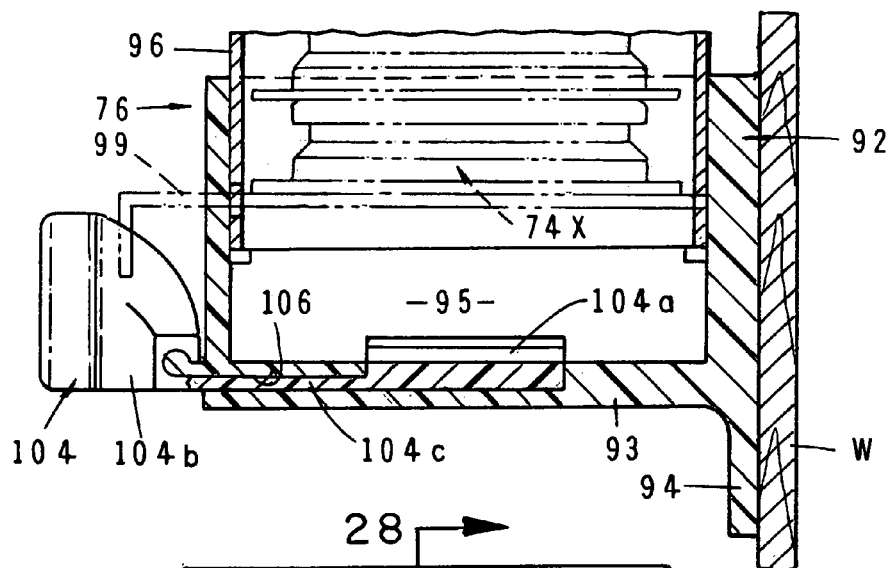
FIG. 26 is a cross-sectional view along lines 26-26 of FIG. 24.
Figure 27:
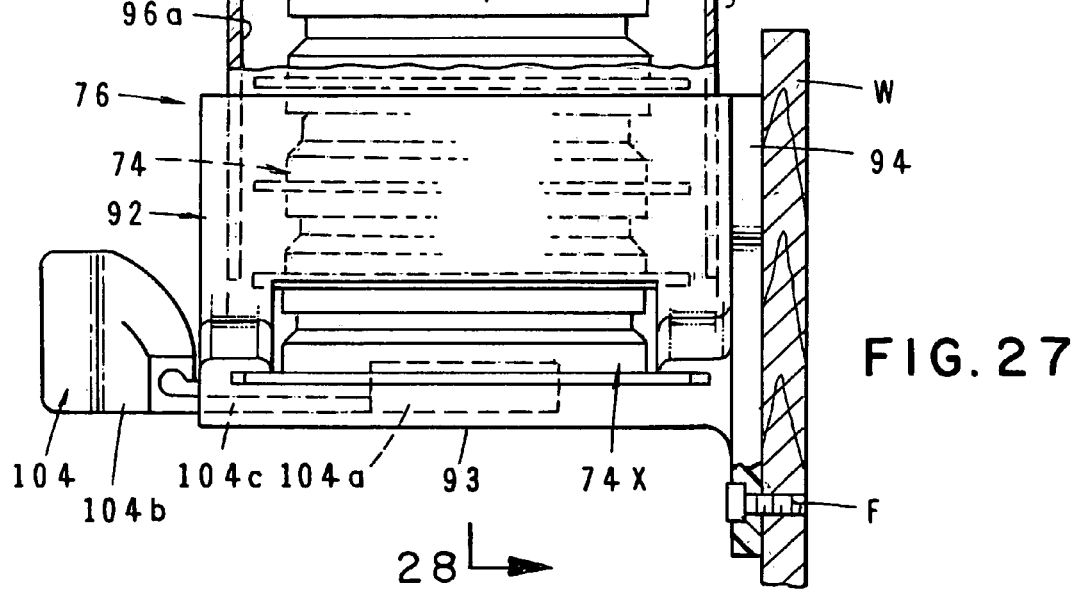
FIG. 27 is a view taken along lines 27-27 of FIG. 24.

Connected to each of the cover-positioning devices 78 to form a cover dispensing unit 74 (see FIG. 29), is a cover assembly 86 that comprises a uniquely constructed disposable cover 88. Disposable cover 88 comprises a thin, yieldably deformable, membrane-like central portion 88a and a peripheral portion 88b. Connected to peripheral portion 88b is an elastomeric bead 90 (FIG. 30) that is removably receivable over rim 84 in the manner best seen in FIG. 30 of the drawings. Considering once again the feed unit 76 of the apparatus of the invention, as illustrated in FIGS. 23 and 24 of the drawings, the feed unit here comprises a base assembly 92 that includes a base 93 having a generally planar forward portion 93a and a rearward portion 93b. Base assembly 92 also includes a downwardly extending rear flange 94 that enables the feed unit to be attached to a vertical wall "W" by conventional screws like fasteners "F" (see FIGS. 26 and 27). Rearward portion 93b is provided with a receiving chamber 95, the purpose of which will presently be described.

Receivable within receiving chamber 95 is an upstanding, hollow dispensing tower 96 having an interior chamber 96a that, in the manner shown in FIGS. 24 and 28, functions to hold the plurality of stacked cover dispensing units 74. To enable the sequential feeding of the cover dispensing units into the receiving chamber 95, the support member 99 that initially supports the stack of cover dispensing units is removed from the lower portion of the dispensing tower 96. In a manner presently to be described, movement of the support member 99 in the direction of the arrow 101 of FIG. 23 permits the sequential feeding of the cover dispensing units into the receiving chamber 95 (see also FIGS. 26 and 27).

For a purpose presently to be described, base 93 is also provided with a guide channel 102 (FIG. 23) that slidably receives the pusher segment 104a of a finger engaging dispenser assembly 104. Assembly 104 also includes a finger engaging knob 104b that is interconnected with pusher segment 104a by a connector segment 104c (FIG. 25). Connector segment 104c is slidable within a guide slot 106 formed in base 93 and is movable within guide slot 106 between a first retracted position shown in FIG. 23 and a second, advanced dispensing position shown in FIGS. 31 and 32. When the finger engaging dispenser knob 104b is moved from its first retracted position to its second dispensing position, the pusher segment 104a of the dispenser assembly engages the cover dispensing unit 74 that resides within receiving chamber 95, such as the device identified in FIG. 23 by the numeral 74x. As the pusher segment 104a advances within guide channel 106, the cover dispensing unit 74x is moved forwardly onto the generally planar forward portion 93a of base 93.

Figure 31:
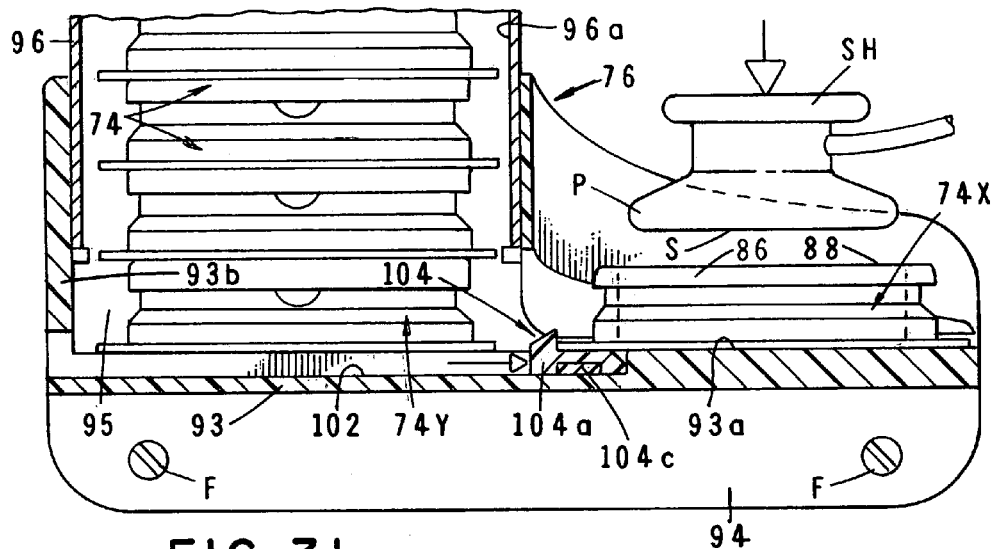
FIG. 31 is a view similar to FIG. 28 illustrating the method of affixing the disposable stethoscope head cover to the stethoscope head.
Figure 32:
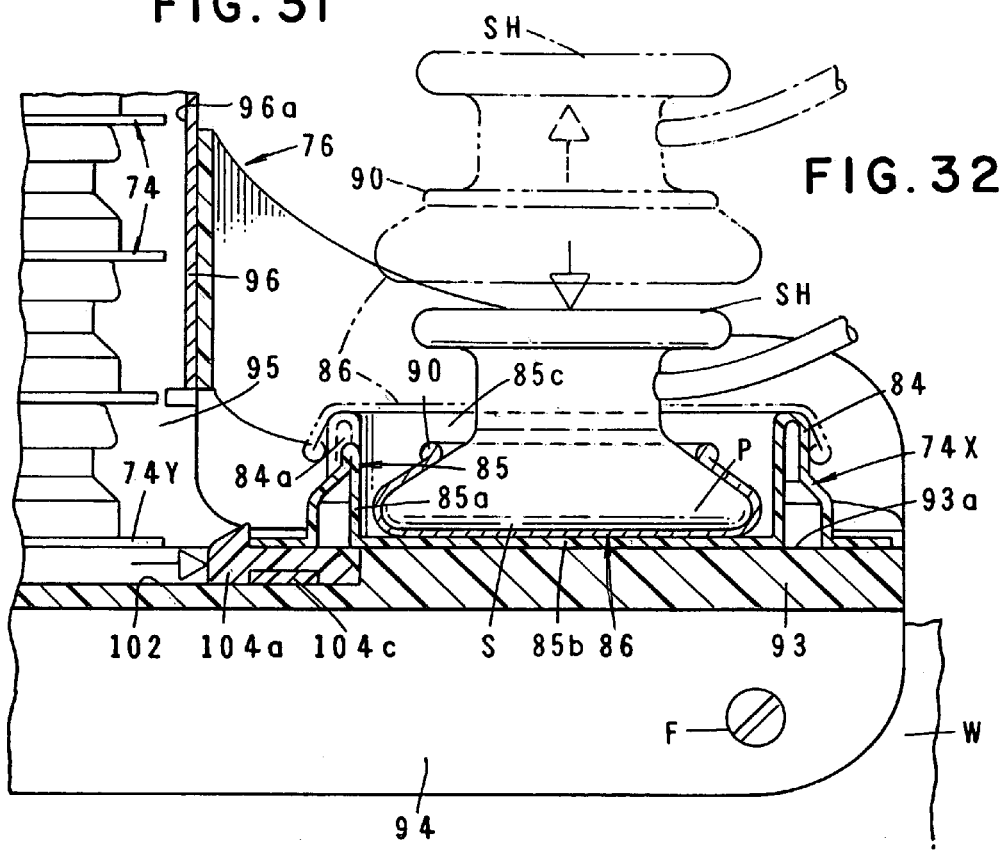
FIG. 32 is a view similar to FIG. 31 further illustrating the method of affixing the disposable stethoscope head cover to the stethoscope head.

With the cover dispensing unit designated as 74x in position on the generally planar forward portion 93a of base 93 in the manner shown in FIGS. 31 and 32, the disposable cover assembly 74 can be interconnected with the stethoscope head in the manner illustrated in FIGS. 31 and 32 of the drawings. More particularly, in order to interconnect the disposable cover with the stethoscope head "SH", the stethoscope head is moved from the position shown in FIG. 31 into a downward position where it is in engagement with the upper surface of the yieldably deformable central portion of the cover 88.

A continued downward movement of the stethoscope head to the position shown by the solid lines in FIG. 32 will cause it to move through the upper portion of the supporting frame and into the stethoscope covered position shown in FIG. 32 of the drawings. As a stethoscope head moves downwardly, the elastomeric bead 90 will release from the rim portion of the base and will move into engagement with the peripheral portion "P" of the stethoscope head "SH", thereby removably securing the cover to the stethoscope head. In this position, the flexible central membrane portion of the cover resides in close engagement with the lower surface "S" of the stethoscope head. Once the cover is in position over the stethoscope head, the assemblage thus formed can be removed from the apparatus in the manner illustrated by the phantom lines in FIG. 32. Following the examination of the patient, the cover assembly 86 can be conveniently removed from the stethoscope head and discarded into a suitable contaminated waste receptacle.

In using this apparatus of the invention, the feed unit 96 is first mated with the base assembly 92 in the manner shown in FIG. 23 of the drawings. This done, movement of the finger engaging dispenser knob 104b from its first retracted position into the position shown in FIG. 23 of the drawings will cause the pusher segment 104a of the finger engaging dispenser knob to engage the cover dispensing unit 74x and move it forwardly within guide channel 102. Further movement of the finger engaging dispenser knob will cause the cover dispensing unit 74x to move into the second outward position wherein it resides on planar portion 93a (see FIG. 31). At the same time, the cover dispensing unit identified in FIGS. 31 and 32 by the numeral 74y will drop downwardly into the position earlier occupied by cover dispensing unit 74x.

Figure 35:
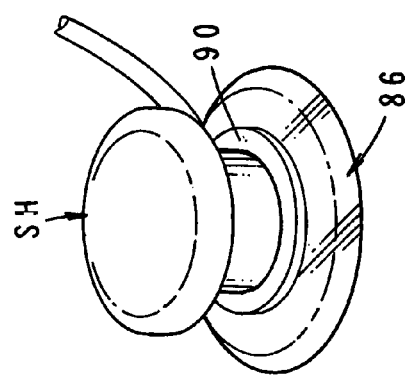
FIG. 35 is a generally perspective view illustrating the appearance of the stethoscope head with the disposable stethoscope head cover affixed thereto.
Figure 40:
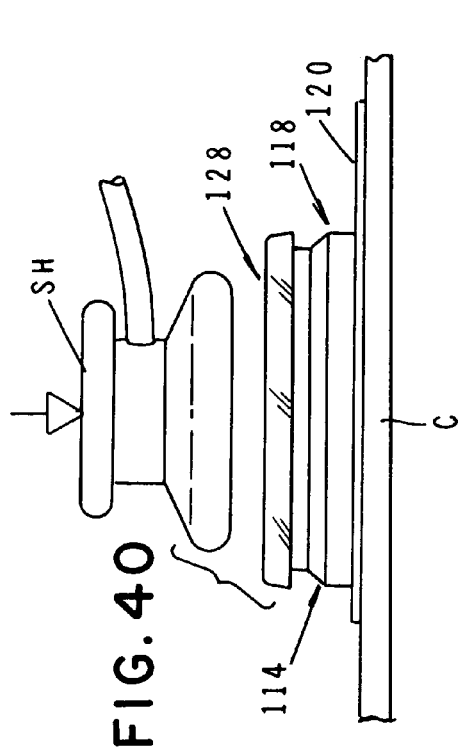
FIG. 40 is an illustrative view illustrating the method of affixing to the stethoscope head the disposable stethoscope head cover that has been removed from the dispensing unit.

With the cover dispensing unit designated as 74y thusly positioned, the stethoscope head is moved from the position shown in FIG. 31 into the downward position shown in FIG. 32 where it is in engagement with the cover assembly 86, and the elastomeric bead 90 removably secures the cover assembly to the stethoscope head (see FIG. 35). Following the examination of the patient, the cover assembly 86 can be conveniently removed from the stethoscope head and discarded into a suitable contaminated waste receptacle. To expedite the removal of the cover assembly 86 from the stethoscope head, the upstanding rim portion 84 is provided with the previously identified generally U-shaped opening 84a into which the index finger can be inserted.

To cover the stethoscope head with a fresh cover assembly 86, finger engaging dispenser knob 104b is returned to its first starting position. As the finger engaging dispenser knob 104b moves rearwardly, the pusher segment 104a slides beneath the fresh cover assembly (see FIG. 34) and then moves into pushing engagement with the fresh cover dispensing unit. Forward movement of the finger engaging dispensing knob 104b from this starting position will cause the pusher segment 104a to move the fresh cover dispensing unit forwardly within guide channel 102 into the second outward position wherein it resides on planar surface 93a. At the same time, the next dispensing unit will fall into the receiving chamber 95 in the manner illustrated in FIGS. 33 and 34. With the fresh cover dispensing unit disposed on planar surface 93a, the cover assembly 86 can be removably affixed to the stethoscope head in the manner previously described.

Turning next to FIGS. 36 through 41, yet another form of the stethoscope head covering apparatus of the present invention is there shown and generally designated by the numeral 112. Apparatus 112 is also similar in many respects to the earlier described embodiments and like numerals are used in FIGS. 36 through 41 to identify like components. Apparatus 112 here comprises a plurality of cover dispensing units 114 of the character illustrated in FIG. 36 of the drawings and a feed unit 116, the character of which will presently be described. As in the earlier described embodiments of the invention, feed unit 116 functions to sequentially dispense the plurality of cover dispensing units 114 that are stacked within the tower portion 116a of the feed unit (FIG. 38).

Figure 36:
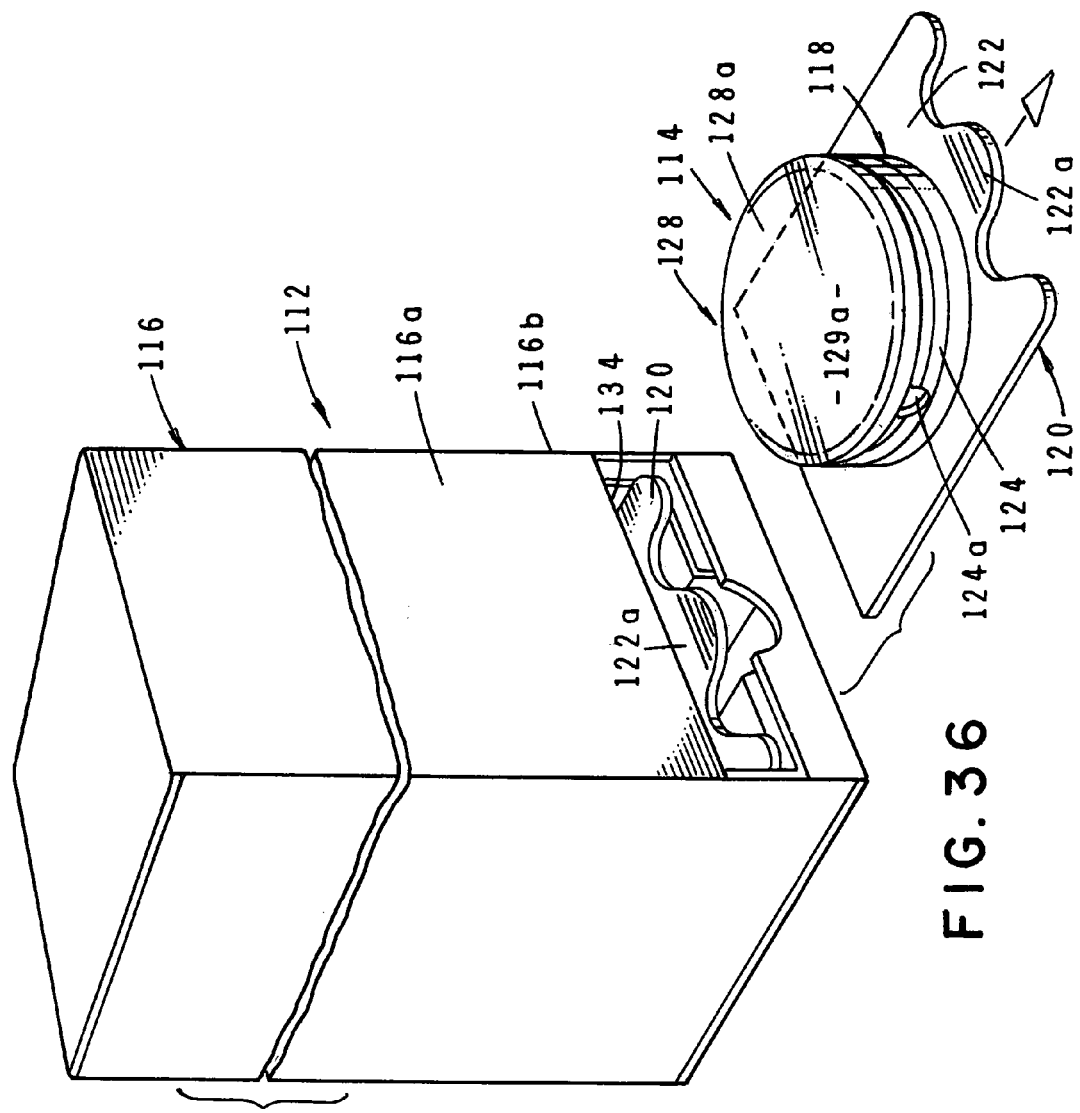
FIG. 36 is a generally perspective, foreshortened view of yet another form of cover positioning device of the invention for interconnecting a disposable stethoscope head cover with a stethoscope head.
Figure 41:
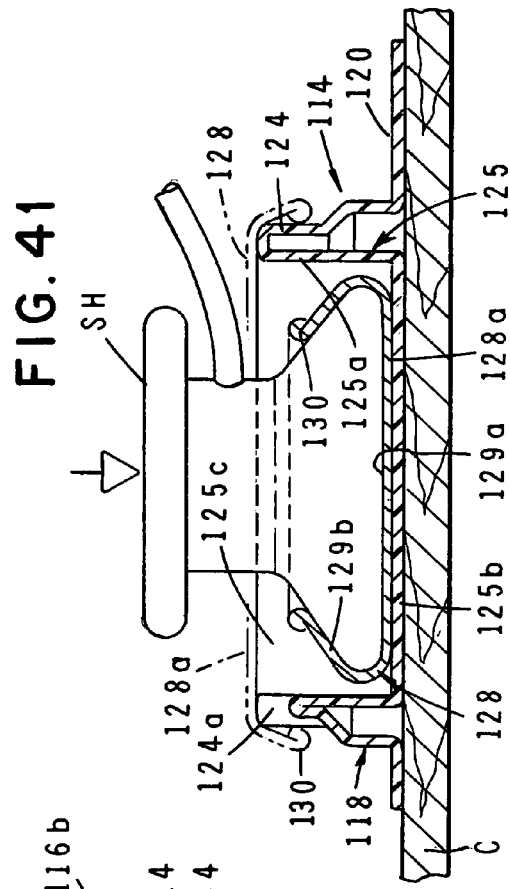
FIG. 41 is a view similar to FIG. 40, further illustrating the method of affixing the disposable stethoscope head cover to the stethoscope head.
Figure 37:
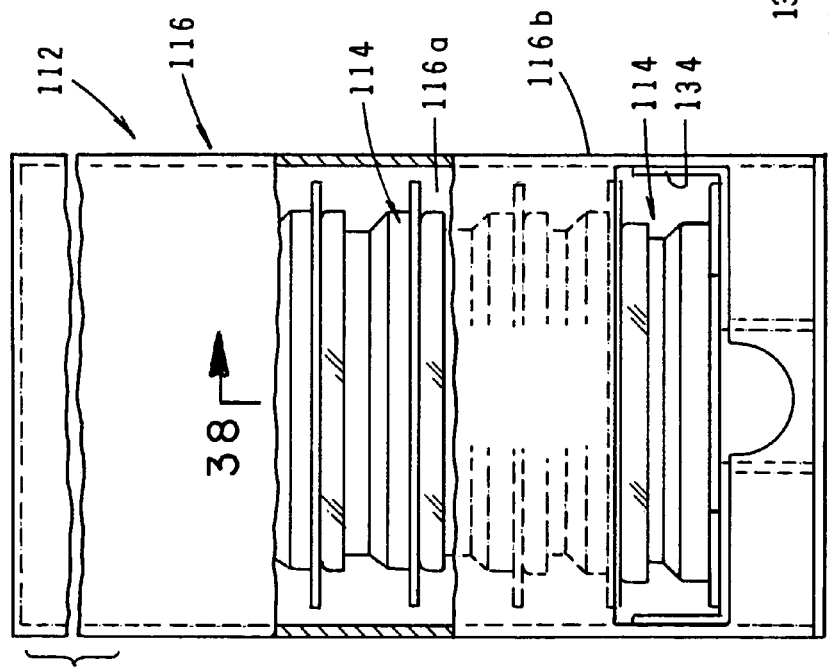
FIG. 37 is a front view of the cover positioning device shown in FIG. 36, the view being partly broken away to show internal construction.
Figure 42:
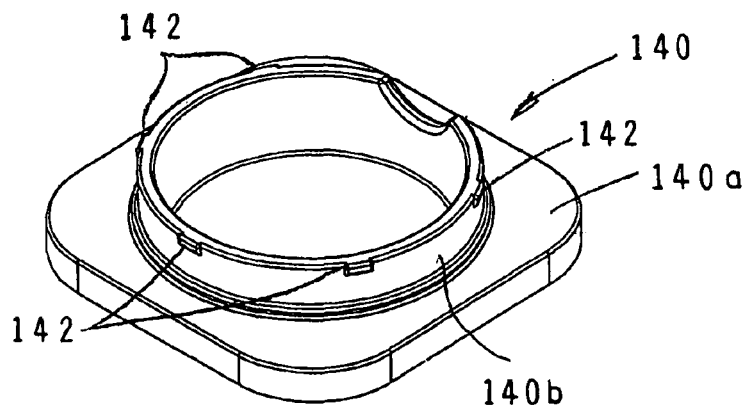
FIG. 42 is a generally perspective view of one form of the cover supporting frame of the invention that supports the disposable stethoscope head cover in position for interconnection with the stethoscope head.

Each of the cover dispensing units 114 comprises a supporting frame 118 that includes a base 120 having a generally planar portion 122, including a finger gripping tab 122a and a upstanding rim 124 that is connected to base 120 in the manner shown in FIGS. 36 and 41. For a purpose presently to be described, rim 124 is provided with a generally U-shaped opening 124a. Rim 124 is also connected to a chamber defining structure 125 that includes an upstanding side wall 125a and a base wall 125b that cooperate with the side wall to define a stethoscope head receiving chamber 125c.

Connected to each of the cover-positioning devices to form a cover dispensing unit 114 (see FIGS. 40 and 41), is a cover assembly 128 that comprises a uniquely constructed disposable cover 128a. Disposable cover 128a comprises a thin, yieldably deformable, membrane-like central portion 129a and a peripheral portion 129b. Connected to peripheral portion 129b is an elastomeric bead 130 that is removably receivable over rim 124 in the manner best seen in FIG. 41 of the drawings. While the cover dispensing unit 114 can be constructed of various materials, a material that has proved quite satisfactory comprises medical grade polyethylene, or an equivalent material. The polyethylene can be clear, colored, or matte. Similarly, disposable cover 128a can be constructed from various materials including any food, or medical grade plastic. A material that has proved quite satisfactory comprises polyolefin. The polyolefin can be clear or colored, as may be desired.

Considering once again the feed unit 116 of the apparatus of this latest form of the invention, as best seen in FIG. 36 of the drawings, the feed unit here comprises a hollow, box like structure that includes a base portion 116b that is provided with an opening 134 through which the cover dispensing units 114 can be sequentially removed.

In using this apparatus of this latest form of the invention, the lowermost cover dispensing unit 114 can be grasped by the fingers of the user and removed from the base portion 116b via the opening 134 (see FIG. 38). Next the dispensing unit is positioned on a planar surface such as the top of a table, or counter "C" (see FIG. 41). With the dispenser unit in this position, the stethoscope head is moved from the position shown in FIG. 40 into the downward position shown in FIG. 41, where it becomes interconnected with the cover assembly 128 and wherein the elastomeric bead 130 removably secures the cover assembly to the stethoscope head (see FIG. 41). Following the examination of the patient, the cover assembly can be conveniently removed from the stethoscope head and discarded into a suitable contaminated waste receptacle. To expedite the removal of the cover assembly from the stethoscope head, the upstanding rim portion 124 is provided with the previously identified generally U-shaped opening 124a into which the index finger can be inserted.

To cover the stethoscope head with a fresh cover assembly, the cover dispensing unit 114 next in sequence can be grasped by the fingers of the user and removed from the base portion 116b via the opening 134. This done, the dispensing unit is once again positioned on a planar surface such as the top of a table or counter, and the cover assembly 128 is interconnected with the stethoscope head in the manner previously described.

Turning next to FIGS. 42 through 49, a number of cover dispensing units of slightly different configurations are there illustrated. For example, the cover dispensing unit 140 illustrated in FIG. 42 of the drawings is similar in many respects to the previously described cover dispensing unit 78 that is illustrated in FIG. 30 of the drawings. However, cover dispensing unit 140 here includes a base 140a that is somewhat thicker and includes a rim portion 140b that is provided with a plurality of circumferentially spaced protuberances 142 that assist in positioning the cover assembly of the device and over which the elastomeric bead of the cover assembly is received.

Figure 43:
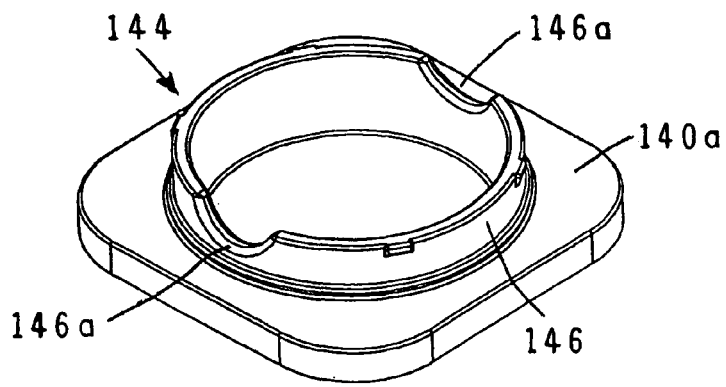
FIG. 43 is a generally perspective view of an alternate form of cover supporting frame of the invention.

FIG. 43 of the drawings illustrates a cover dispensing unit 144 that is similar in many respects to the previously described cover dispensing unit 140. However, the rim portion 146 of the dispensing unit 144 is provided with a pair of oppositely disposed, generally U-shaped openings 146a that serve to expedite removal of the cover assembly of the device following the examination of the patient.

Figure 44:
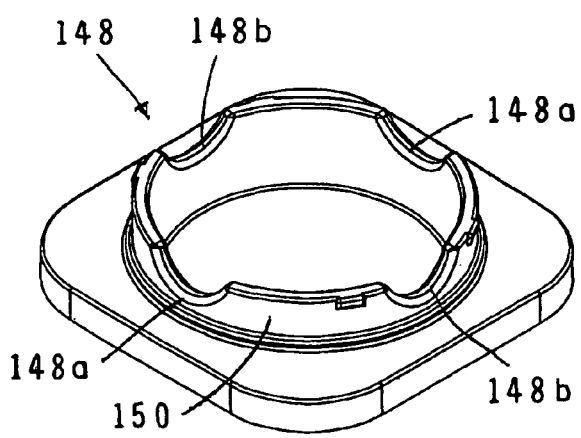
FIG. 44 is a generally perspective view of still another form of cover supporting frame of the invention.

FIG. 44 of the drawings illustrates a cover dispensing unit 148 that is also similar in many respects to the previously described cover dispensing unit 140. However, the rim portion 150 of the dispensing unit 148 is provided with two pair of oppositely disposed, generally U-shaped openings 148a and 148b that serve to expedite removal of the cover assembly of the device following the examination of the patient.

Figure 45:
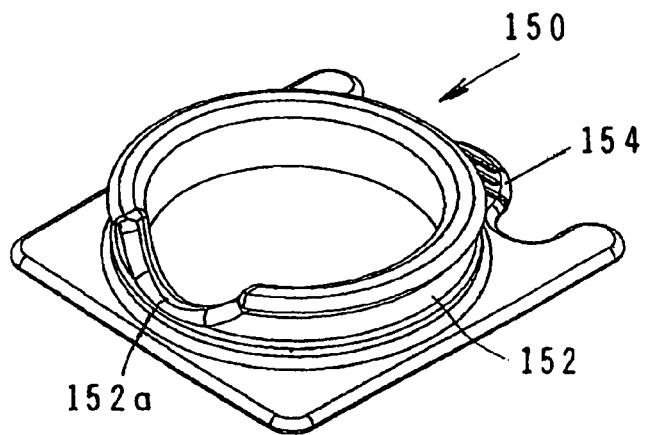
FIG. 45 is a generally perspective view of still another form of cover supporting frame of the invention that has a slightly different base configuration.

FIG. 45 of the drawings illustrates a cover dispensing unit 150 that is similar in many respects to the previously described supporting frame 118 illustrated in FIG. 36 of the drawings. However, the rim portion 152 of the dispensing unit 150 is provided with a generally U-shaped opening 152a that, unlike frame 118, is located opposite the finger engaging tab 154 of the unit.

Figure 46:
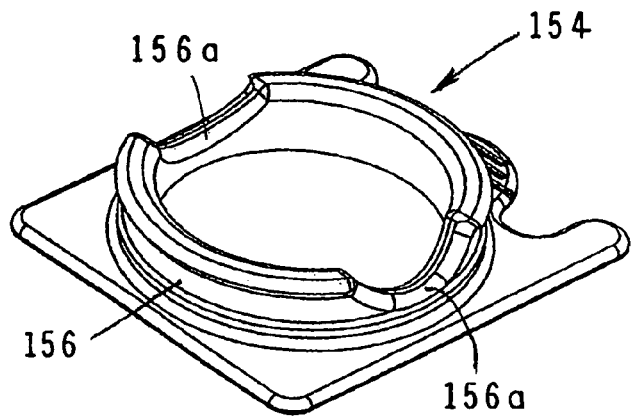
FIG. 46 is a generally perspective view of yet another form of cover supporting frame of the invention that has a slightly different base configuration.

FIG. 46 of the drawings illustrates a cover dispensing unit 154 that is similar in many respects to the previously described cover dispensing unit 150. However, the rim portion 156 of the dispensing unit 154 is provided with a pair of oppositely disposed, generally U-shaped openings 156a that serve to expedite removal of the cover assembly of the device following the examination of the patient.

Figure 47:
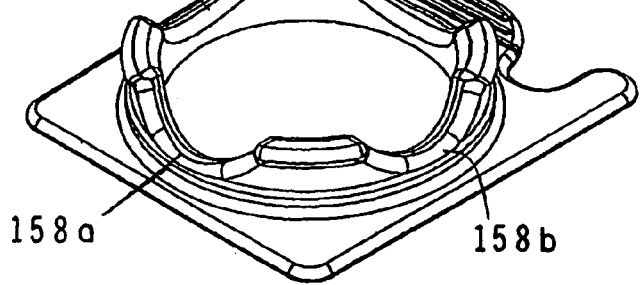
FIG. 47 is a generally perspective view of still another form of cover supporting frame of the invention that has a slightly different base configuration.

FIG. 47 of the drawings illustrates a cover dispensing unit 158 that is also similar in many respects to the previously described cover dispensing unit 150. However, the rim portion 160 of the dispensing unit 158 is provided with two pair of oppositely disposed, generally U-shaped openings 158a and 158b that serve to expedite removal of the cover assembly of the device following the examination of the patient.

Figure 48:
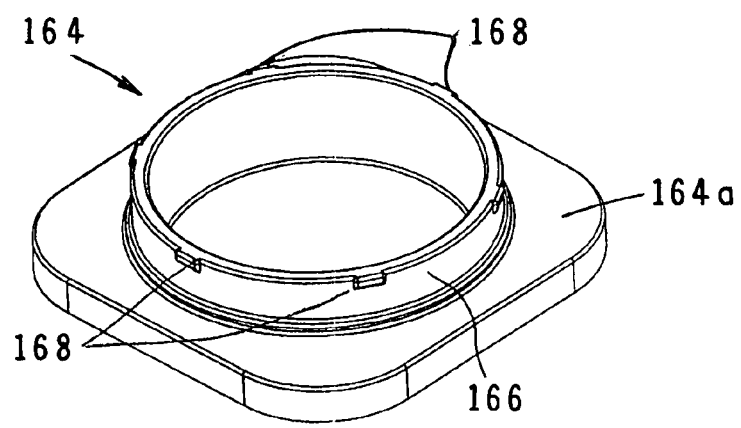
FIG. 48 is a generally perspective view of yet another form of cover supporting frame of the invention that has a slightly different rim configuration.

FIG. 48 of the drawings illustrates a dispensing unit 164 that is also similar in many respects to the previously described cover dispensing unit 78 that is illustrated in FIG. 30 of the drawings. However, cover dispensing unit 164 here includes a base 164a that is somewhat thicker and, while the rim portion 166 of the unit is provided with a plurality of circumferentially spaced protuberances 168, it has no generally U-shaped openings formed therein.

Figure 49:
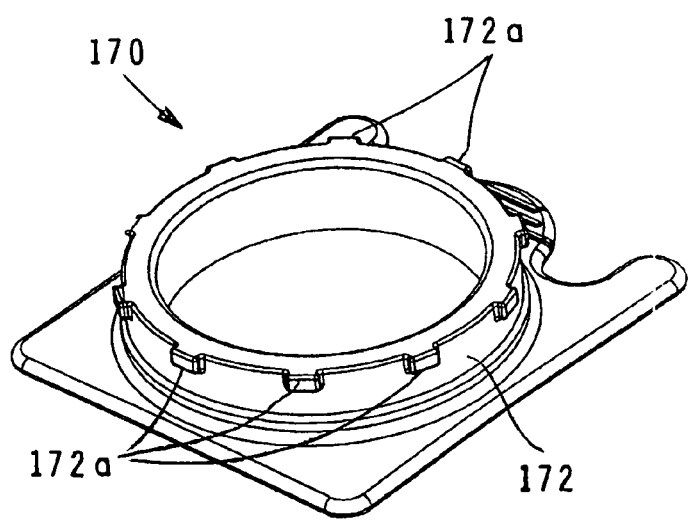
FIG. 49 is a generally perspective view of still another form of cover supporting frame of the invention that has a slightly different base and a slightly different rim configuration.

FIG. 49 of the drawings illustrates a cover dispensing unit 170 that is similar in many respects to the previously described supporting frame 118 illustrated in FIG. 36 of the drawings. However, while the rim portion 172 of the dispensing unit 170 is provided with a plurality of circumferentially spaced protuberances 172a, it has no generally U-shaped openings formed therein.

Having now described the invention in detail in accordance with the requirements of the patent statutes, those skilled in this art will have no difficulty making changes and modifications in the individual parts or their relative assembly in order to meet specific requirements or conditions. Such changes and modifications may be made without departing from the scope and spirit of the invention, as set forth in the following claims.

The invention claimed is:

1. A stethoscope head covering apparatus comprising:
  (a) a plurality of cover-positioning devices, each cover-positioning device comprising:
    (i) a positioning base having a generally planar portion and an upstanding rim connected to said generally planar portion, said rim defining an opening;
    (ii) an upstanding side wall connected to said rim; and
    (iii) a base wall connected to said upstanding side wall, said side wall and said base wall cooperating to define a stethoscope head receiving chamber;
  (b) a cover assembly connected to each of said plurality of cover-positioning devices to form a plurality of cover dispensing units each said cover assembly comprising:
    (i) a disposable cover having a central portion comprising a membrane and a peripheral portion; and
    (ii) an elastomeric bead connected to said peripheral portion of said cover, said elastomeric bead being removably connected to said upstanding rim; and
  (c) a feed unit for sequentially dispensing said plurality of cover dispensing units, said feed unit comprising:
    (i) a base assembly including:
      a. a base having a guide channel and a receiving chamber;
      b. a pusher segment movable within said guide channel of said base for movement between a first retracted position and a second dispensing position; and
    (ii) a dispensing tower receivable within said receiving chamber of said base assembly for holding said plurality of cover dispensing units.

2. The apparatus as defined in claim 1 in which said base of said base assembly is provided with a guide slot and in which said base assembly further includes:
  (a) a connector segment connected with said pusher segment, said connector segment being slidable within said guide slot between a first retracted position and a second, advanced dispensing position; and
  (b) a finger engaging knob connected to said connector segment.

3. A stethoscope head covering apparatus comprising:
  (a) a cover-positioning device comprising a positioning base having a generally planar portion and a rim connected to said generally planar portion, said rim defining an opening, said cover positioning device further comprising:
    (i) an upstanding side wall connected to said rim; and
    (ii) a base wall connected to said upstanding side wall, said side wall and said base wall cooperating to define a stethoscope head receiving chamber; and
  (b) a cover assembly connected to said cover-positioning device to form a cover dispensing unit comprising:
    (i) a disposable cover having a central portion and a peripheral portion; and
    (ii) an elastomeric bead connected to said peripheral portion of said cover, said elastomeric bead being removably connected to said rim of said cover-positioning device.

4. A stethoscope head covering apparatus comprising:
  (a) a cover-positioning device comprising a positioning base having a generally planar portion and a rim, said rim having a plurality of circumferentially spaced protuberances and connected to said generally planar portion, and defining an opening; and (b) a cover assembly connected to said cover-positioning device to form a cover dispensing unit comprising:
  (i) a disposable cover having a central portion and a peripheral portion; and
  (ii) an elastomeric bead connected to said peripheral portion of said cover, said elastomeric bead being removably connected to said rim of said cover-positioning device.

5. A stethoscope head covering apparatus comprising:
(a) a plurality of cover-positioning devices, each cover-positioning device comprising a positioning base having a generally planar portion and an upstanding rim connected to said generally planar portion, said rim defining an opening, each of said plurality of cover positioning devices further comprising an upstanding side wall connected to said rim and a base wall connected to said upstanding side wall, said side wall and said base wall cooperating to define a stethoscope head receiving chamber;
(b) a cover assembly connected to each of said plurality of cover-positioning devices to form a plurality of cover dispensing units each said cover assembly comprising:
  (i) a disposable cover having a central portion comprising a membrane and a peripheral portion; and
  (ii) an elastomeric bead connected to said peripheral portion of said cover, said elastomeric bead being removably connected to said upstanding rim of a selected one of said plurality of cover-positioning devices; and
(c) a feed unit for sequentially dispensing said plurality of cover dispensing units.

6. A stethoscope head covering apparatus comprising:
(a) a plurality of cover-positioning devices, each cover-positioning device comprising a positioning base having a finger gripping tab and a generally planar portion and an upstanding rim connected to said generally planar portion, said rim defining an opening;
(b) a cover assembly connected to each of said plurality of cover-positioning devices to form a plurality of cover dispensing units each said cover assembly comprising:
  (i) a disposable cover having a central portion comprising a membrane and a peripheral portion; and
  (ii) an elastomeric bead connected to said peripheral portion of said cover, said elastomeric bead being removably connected to said upstanding rim of a selected one of said plurality of cover-positioning devices; and
(c) a feed unit for sequentially dispensing said plurality of cover dispensing units.

7. A stethoscope head covering apparatus comprising:
(a) a plurality of cover-positioning devices, each cover-positioning device comprising a positioning base having a generally planar portion and an upstanding rim, said rim including a plurality of circumferentially spaced protuberances and being connected to said generally planar portion and defining an opening;
(b) a cover assembly connected to each of said plurality of cover-positioning devices to form a plurality of cover dispensing units each said cover assembly comprising:
  (i) a disposable cover having a central portion comprising a membrane and a peripheral portion; and
  (ii) an elastomeric bead connected to said peripheral portion of said cover, said elastomeric bead being removably connected to said upstanding rim of a selected one of said plurality of cover-positioning devices; and
(c) a feed unit for sequentially dispensing said plurality of cover dispensing units.

8. A stethoscope head covering apparatus comprising:
(a) a cover-positioning device comprising a positioning base having a generally planar portion and a rim connected to said generally planar portion, said rim defining a generally U-shaped opening; and
(b) a cover assembly connected to said cover-positioning device to form a cover dispensing unit comprising:
  (i) a disposable cover having a central portion and a peripheral portion; and
  (ii) an elastomeric bead connected to said peripheral portion of said cover, said elastomeric bead being removably connected to said upstanding rim of said cover-positioning device.

9. A stethoscope head covering apparatus comprising:
(a) a cover-positioning device comprising a positioning base having a generally planar portion and a rim connected to said generally planar portion, said rim defining an opening; and
(b) a cover assembly connected to said cover-positioning device to form a cover dispensing unit comprising:
  (i) a disposable cover having a central portion and a peripheral portion; and
  (ii) an elastomeric bead connected to said peripheral portion of said cover, said elastomeric bead being removably connected to said rim of said cover-positioning device; and
(c) a feed unit for holding a plurality of cover dispensing units, said feed unit comprising a hollow structure that includes a base portion provided with an opening through which the cover dispensing units can be sequentially removed.

10. A stethoscope head covering apparatus comprising:
(a) a cover-positioning device comprising a positioning base having a generally planar portion and a rim connected to said generally planar portion, said rim defining a generally U-shaped opening;
(b) a cover assembly connected to said cover-positioning device to form a cover dispensing unit comprising:
  (i) a disposable cover having a central portion and a peripheral portion; and
  (ii) an elastomeric bead connected to said peripheral portion of said cover, said elastomeric bead being removably connected to said upstanding rim of said cover-positioning device; and
(c) a feed unit for dispensing said cover dispensing unit, said feed unit comprising:
  (i) a base assembly including a guide slot and:
    a. a base having a guide channel, a receiving chamber and a downwardly extending flange for attaching said feed unit to a vertical wall;
    b. a pusher segment movable within said guide channel of said base between a first retracted position and a second dispensing position; and
    c. a connector segment connected to said pusher segment, said connector segment being slidable within said guide slot between a first retracted position and a second, advanced dispensing position; and
  (ii) a dispensing tower receivable within said receiving chamber of said base assembly.

11. A stethoscope head covering apparatus comprising:
(a) a plurality of cover-positioning devices, each cover-positioning device comprising a positioning base having a generally U-shaped opening, a generally planar portion and an upstanding rim connected to said generally planar portion, said rim defining an opening;

(b) a cover assembly connected to each of said plurality of cover-positioning devices to form a plurality of cover dispensing units, each said cover assembly comprising:
   (i) a disposable cover having a central portion comprising a membrane and a peripheral portion; and
   (ii) an elastomeric bead connected to said peripheral portion of said cover, said elastomeric bead being removably connected to said upstanding rim of a selected one of said plurality of cover-positioning devices; and (c) a feed unit for sequentially dispensing said plurality of cover dispensing units.

* * * * *